US009439959B2

(12) United States Patent
Haynes

(10) Patent No.: US 9,439,959 B2
(45) Date of Patent: Sep. 13, 2016

(54) CHIMERIC INFLUENZA VIRUS-LIKE PARTICLES

(75) Inventor: Joel R. Haynes, Bozeman, MT (US)

(73) Assignee: TAKEDA VACCINES, INC., Bozeman, MT (US)

( * ) Notice: Subject to any disclaimer, the term of this patent is extended or adjusted under 35 U.S.C. 154(b) by 1116 days.

(21) Appl. No.: 12/375,376

(22) PCT Filed: Jul. 27, 2007

(86) PCT No.: PCT/US2007/016900
§ 371 (c)(1),
(2), (4) Date: Nov. 17, 2009

(87) PCT Pub. No.: WO2008/094197
PCT Pub. Date: Aug. 7, 2008

(65) Prior Publication Data
US 2010/0074915 A1   Mar. 25, 2010

Related U.S. Application Data

(60) Provisional application No. 60/878,920, filed on Jan. 5, 2007, provisional application No. 60/834,200, filed on Jul. 27, 2006.

(51) Int. Cl.
| | |
|---|---|
| *A61K 39/145* | (2006.01) |
| *A61K 39/12* | (2006.01) |
| *C07K 14/005* | (2006.01) |
| *A61K 39/385* | (2006.01) |
| *A61K 39/39* | (2006.01) |
| *A61K 39/00* | (2006.01) |

(52) U.S. Cl.
CPC ............. *A61K 39/145* (2013.01); *A61K 39/12* (2013.01); *A61K 39/385* (2013.01); *A61K 39/39* (2013.01); *C07K 14/005* (2013.01); *A61K 2039/5258* (2013.01); *A61K 2039/543* (2013.01); *A61K 2039/55516* (2013.01); *A61K 2039/55572* (2013.01); *A61K 2039/55583* (2013.01); *A61K 2039/58* (2013.01); *A61K 2039/6068* (2013.01); *A61K 2039/6075* (2013.01); *C07K 2319/735* (2013.01); *C12N 2740/10022* (2013.01); *C12N 2740/13022* (2013.01); *C12N 2740/13023* (2013.01); *C12N 2740/16122* (2013.01); *C12N 2760/16122* (2013.01); *C12N 2760/16123* (2013.01); *C12N 2760/16134* (2013.01)

(58) Field of Classification Search
CPC C07K 14/005; C07K 14/11; C07K 16/1018; A61K 39/12; A61K 2039/5258; A61K 39/145; A61K 39/00; A61K 2039/70; A61K 39/21; A61K 2039/5256; A61K 35/76; A61K 2039/6075; A61K 38/162; C12N 7/00; C12N 2760/16123; C12N 2760/16223; C12N 2760/16234; C12N 15/86; C12N 2810/6072

See application file for complete search history.

(56) References Cited

U.S. PATENT DOCUMENTS

| | | | |
|---|---|---|---|
| 6,099,847 A | 8/2000 | Tobin et al. | |
| 6,602,705 B1 * | 8/2003 | Barnett et al. | ............. 435/320.1 |
| 7,404,963 B2 | 7/2008 | Sotomayor et al. | |
| 8,574,590 B2 * | 11/2013 | Doranz et al. | ............. 424/204.1 |
| 2003/0049607 A1 | 3/2003 | Greener et al. | |
| 2003/0165521 A1 * | 9/2003 | Smith | .................... A61K 39/12 424/186.1 |
| 2003/0198621 A1 | 10/2003 | Megede et al. | |
| 2003/0223964 A1 * | 12/2003 | Barnett | ................ C07K 14/005 424/93.2 |
| 2004/0071661 A1 | 4/2004 | Klatzmann et al. | |
| 2004/0105871 A1 * | 6/2004 | Robinson et al. | ......... 424/199.1 |
| 2005/0123563 A1 | 6/2005 | Doranz et al. | |
| 2005/0186621 A1 * | 8/2005 | Galarza et al. | .................... 435/6 |
| 2006/0088555 A1 | 4/2006 | Sotomayor et al. | |
| 2006/0216702 A1 | 9/2006 | Compans et al. | |
| 2006/0263804 A1 | 11/2006 | Robinson et al. | |
| 2007/0184526 A1 * | 8/2007 | Smith et al. | .................. 435/69.1 |
| 2008/0261271 A1 * | 10/2008 | Barnett et al. | ............... 435/69.1 |
| 2010/0047266 A1 * | 2/2010 | Haynes | ..................... 424/186.1 |
| 2010/0239610 A1 * | 9/2010 | D'Aoust et al. | ........... 424/210.1 |
| 2011/0195113 A1 * | 8/2011 | Richardson et al. | ......... 424/450 |

FOREIGN PATENT DOCUMENTS

| | | | |
|---|---|---|---|
| CA | 2486282 A1 | * | 5/2004 |
| JP | 2001-504702 A | | 4/2001 |
| JP | 2004/501647 A | | 1/2004 |
| JP | 2006-502704 A | | 1/2006 |
| WO | 98/23735 A1 | | 6/1998 |
| WO | 99/33868 A2 | | 7/1999 |
| WO | 2001-527091 A | | 12/2001 |
| WO | 02/000693 A2 | | 1/2002 |
| WO | 02/00865 A2 | | 1/2002 |
| WO | 2003/066868 A1 | | 8/2003 |
| WO | 03/097675 A1 | | 11/2003 |
| WO | 2004/000351 A1 | | 12/2003 |

(Continued)

OTHER PUBLICATIONS

Jin et al. Influenza virus hemagglutinin and neuraminidase cytoplasmic tails control particle shape. The EMBO Journal 1997, vol. 16, No. 6, pp. 1236-1247.*

(Continued)

*Primary Examiner* — Rachel B Gill
(74) *Attorney, Agent, or Firm* — Morrison & Foerster LLP

(57) ABSTRACT

Chimeric Influenza virus-like particles including gag polypeptides are described. Virus-like particles are generated with a gag polypeptide, a neuraminidase polypeptide and optionally a hemagglutinin polypeptide. Preferred methods of generation include expression in insect cells.

47 Claims, 9 Drawing Sheets

(56) References Cited

FOREIGN PATENT DOCUMENTS

| WO | WO-2004/042001 A2 | 5/2004 |
|---|---|---|
| WO | 2004/046176 A1 | 6/2004 |
| WO | WO 2007047831 A2 * | 4/2007 |
| WO | 2007/075741 A2 | 7/2007 |

OTHER PUBLICATIONS

Lantham et al. Formation of Wild-Type and Chimeric Influenza Virus-Like Particles following Simultaneous Expression of Only Four Structural Proteins. Journal of Virology 2001, vol. 75, No. 13, pp. 6154-6165.*
Quan FS, Huang C, Compans RW, Kang SM. Virus-like particle vaccine induces protective immunity against homologous and heterologous strains of influenza virus. J Virol. Apr. 2007;81(7):3514-24. Epub Jan. 24, 2007.*
Chen BJ, Leser GP, Morita E, Lamb RA. Influenza virus hemagglutinin and neuraminidase, but not the matrix protein, are required for assembly and budding of plasmid-derived virus-like particles. J Virol. Jul. 2007;81(13):7111-23. Epub May 2, 2007.*
Gillis JS. An avian influenza vaccine for humans targeting the polymerase B2 protein inside the capsid instead of hemagglutinin or neuramidase on the virus surface. Med Hypotheses. 2006;66(5):975-7. Epub Jan. 5, 2006.*
Young KR, McBurney SP, Karkhanis LU, Ross TM. Virus-like particles: designing an effective AIDS vaccine. Methods. Sep. 2006;40(1):98-117.*
Chackerian B. Virus-like particles: flexible platforms for vaccine development. Expert Rev Vaccines. Jun. 2007;6(3):381-90.*
CDC. "Vaccine effectiveness—how well does the flu vaccine work?". http://www.cdc.gov/flu/about/qa/vaccineeffect.htm. Rev. Jan. 31, 2014.*
Yao Q, Zhang R, Guo L, Li M, Chen C. Th cell-independent immune responses to chimeric hemagglutinin/simian human immunodeficiency virus-like particles vaccine. J Immunol. Aug. 1, 2004;173(3):1951-8.*
Guo L, Lu X, Kang SM, Chen C, Compans RW, Yao Q. Enhancement of mucosal immune responses by chimeric influenza HA/SHIV virus-like particles. Virology. Sep. 1, 2003;313(2):502-13.*
Extended European Search Report received for EP Patent Application No. 07872585.0, mailed on Aug. 5, 2010, 5 pages.
Bosch et al., "Inhibition of release of lentivirus particles with incorporated human influenza virus haemagglutinin by binding to sialic acid-containing cellular receptors", Journal of General Virology, vol. 82, 2001, pp. 2485-2494.
Guo et al., "Enhancement of mucosal immune responses by chimeric influenza HA/SHIV virus-like particles", Virology, vol. 313, 2003, pp. 502-513.
International Preliminary Report on Patentability received for PCT Patent Application No. PCT/US2007/016900, issued on Jan. 27, 2009, 4 pages.
Zurbriggen, Rinaldo, "Immunostimulating reconstituted influenza virosomes", Vaccine, vol. 21, 2003, pp. 921-924.
De Filette, M. et al. (2005). "Universal Influenza A Vaccine: Optimization of M2-Based Constructs," *Virology* 337:149-161.
Gerhard, W. et al. (Apr. 2006). "Prospects for Universal Influenza Virus Vaccine," *Emerging Infectious Diseases* 12(4):569-574.
International Search Report and Written Opinion mailed Jul. 21, 2008, for PCT Application No. PCT/US07/16900 filed Jul. 27, 2007, 11 pages.
Sambhara, S. et al. (2001). "Heterosubtypic Immunity Against Human Influenza A Viruses, Including Recently Emerged Avian H5 and H9 Viruses, Induced by FLU-ISCOM Vaccine in Mice Requires Both Cytotoxic T-Lymphocyte and Macrophage Function," *Cellular Immunology* 211:143-153.
Takada, A. et al. (2003). "Intranasal Immunization with Formalin-Inactivated Virus Vaccine Induces a Broad Spectrum of Heterosubtypic Immunity Against Influenza A Virus Infection in Mice," *Vaccine* 21:3212-3218.

Office Action received for Japanese Patent Application No. 2009-521850, mailed Aug. 7, 2012, 14 pages (8 pages of English translation and 6 pages of Office Action).
Neirynck et al., "A Universal Influenza A Vaccine Based on the Extracellular Domain of the M2 Protein", Nature Medicine, vol. 5, No. 10, Oct. 1999, pp. 1157-1163.
Office Action received for Australian Patent Application No. 2007345768, issued on Jun. 22, 2012, 4 pages.
International Search Report and Written Opinion received for PCT Patent Application No. PCT/US2007/016938, mailed on Jul. 14, 2008, 8 pages.
International Preliminary Report on Patentability received for PCT Patent Application No. PCT/US2007/016938, issued on Jan. 27, 2009, 8 pages.
Office Action Received for European Patent Application No. 07872585.0, mailed on Dec. 23, 2014, 4 pages.
Extended European Search Report received for European Patent Application No. 07872588.4, mailed on Mar. 16, 2011, 11 pages.
Office Action received for European Patent Application No. 07872588.4, mailed on Dec. 17, 2012, 6 pages.
Office Action received for Australian Patent Application No. 2007345682, mailed on Jun. 4, 2012, 3 pages.
Notice of Acceptance received for Australian Patent Application No. 2007345768, mailed on Jul. 17, 2013, 2 pages.
Office Action received for Canadian Patent Application No. 2,657,955, mailed on May 13, 2013, 5 pages.
Office Action Received for Canadian Patent Application No. 2,657,955, mailed on May 14, 2014, 3 pages.
Office Action received for Canadian Patent Application No. 2,659,275 mailed on May 13, 2013, 3 pages.
Office Action Received for Canadian Patent Application No. 2,659,275, mailed on May 14, 2014, 2 pages.
Office Action Received for Japanese Patent Application No. 2009-521850, mailed on Jun. 24, 2014, 16 pages(10 pages of English Translation & 6 pages of Official Copy).
Office Action Received for Japanese Patent Application No. 2009-521850, mailed on Nov. 11, 2014, 2 pages of Official Copy Only (See Communication under 37 CFR § 1.98(a) (3)).
Office Action received for Japanese Patent Application No. 2009-521850, mailed on Oct. 22, 2013, 19 pages (12 pages of English Translation and 7 pages of official copy).
Office Action received for Japanese Patent Application No. 2009-521858, mailed on Aug. 7, 2012, 14 pages (8 pages of English Translation and 6 pages of Office Action).
Office Action received for Japanese Patent Application No. 2009-521858, mailed on Oct. 15, 2013, 13 pages (8 pages of English Translation and 5 pages of Office Action).
Final Office Action received for U.S. Appl. No. 12/375,281, mailed on Aug. 7, 2012, 15 pages.
Non Final Office Action received for U.S. Appl. No. 12/375,281, mailed on Feb. 14, 2012, 19 pages.
Non-Final Office Action received for U.S. Appl. No. 12/375,281, mailed on Jan. 30, 2014, 16 pages.
Alce et al., "APOBEC3G Is Incorporated into Virus-like Particles by a Direct Interaction with HIV-1 Gag Nucleocapsid Protein", The Journal of Biological Chemistry, vol. 279, No. 33, 2004, pp. 34083-34086.
Bellier et al., "DNA Vaccines Encoding Retrovirus-Based Virus-Like Particles Induce Efficient Immune Responses Without Adjuvant", Vaccine, vol. 24, 2006, pp. 2643-2655.
Breun et al., "Protection of MLV Vector Particles From Human Complement", Biochemical and Biophysical Research Communications, vol. 264, No. 1, 1999, pp. 1-5.
Briggs et al., "Do Lipid Rafts Mediate Virus Assembly and Pseudotyping?", Journal of General Virology, vol. 84, 2003, pp. 757-768.
Douaisi et al., "HIV-1 and MLV Gag Proteins are Sufficient to Recruit APOBEC3G into Virus-Like Particles", Biochemical and Biophysical Research Communications, vol. 321, 2004, pp. 566-573.
Harder et al., "Lipid Domain Structure of the Plasma Membrane Revealed by Patching of Membrane Components", The Journal of Cell Biology, vol. 141, No. 4, May 18, 1998, pp. 929-942.

(56) References Cited

OTHER PUBLICATIONS

Krammer et al., "Alternative Influenza Vaccines Made by Insect Cells", Trends in Molecular Medicine, vol. 16, No. 7, 2010, pp. 313-320.

Lipatov et al., "Efficacy of H5 Influenza Vaccines Produced by Reverse Genetics in a Lethal Mouse Model", The Journal of Infections Disease, vol. 191, Apr. 15, 2005, pp. 1216-1220.

Metzner et al., "Rafts, Anchors and Viruses—A role for Glycosylphosphatidylinositol Anchored Proteins in the Modification of Enveloped Viruses and Viral Vectors", Virology, vol. 382, 2008, pp. 125-131.

Pickl et al., "Lipid Rafts and Pseudotyping", Journal of Virology, American Society for General Microbiology, vol. 75, No. 15, Aug. 2001, pp. 7175-7183.

Simons et al., "Lipid Rafts and Signal Transduction", Nature Reviews, Molecular Cell Biology, vol. 1, Oct. 2000, pp. 31-39.

Bogerd et al., "A Single Amino Acid difference in the Host APOBEC3G Protein Controls the Primate Species Specificity of HIV type 1 Virion Infectivity Factor", PNAS, vol. 101, No. 11, Mar. 16, 2004, pp. 3770-3774.

Bright et al., "Influenza Virus like Particles Elicit Broader Immune Responses than Whole Virion Inactivated Influenza Virus or Recombinant Hemagglutinin", Vaccine, vol. 25, 2007, pp. 3871-3878.

Hatziioannou et al., "Retroviral Display of Functional Binding Domains Fused to the Amino Terminus of Influenza Hemagglutinin", Human Gene Therapy, vol. 10, Jun. 10, 1999, pp. 1533-1544.

Haynes et al., "Influenza-Pseudotyped Gag Virus-like Particle Vaccines provide Broad Protection against highly Pathogenic Avian Influenza Challenge", Vaccine, vol. 27, 2009, pp. 530-541.

Haynes, Joel R., "Influenza Virus-Like Particle Vaccines", Expert Review of Vaccines, vol. 8, No. 4, Apr. 2009, pp. 435-445.
Johansson et al., "Supplementation of Conventional Influenza A Vaccine with Purified Viral Neuraminidase Results in a Balanced and Broadened Immune Response", Vaccine, vol. 16, No. 9/10, 1998, pp. 1009-1015.
Khan et al., "Encapsidation of APOBEC3G into HIV-1 Virions Involves Lipid Raft Association and does not Correlate with APOBEC3G Oligomerization", Retrovirology, vol. 6, No. 99, 2009, pp. 1-12.
Pushko et al., "Influenza Virus-like particles comprised of the HA, NA, and M1 Proteins of H9N2 Influenza Virus Induce Protective Immune Responses in BALB/c Mice", Vaccine, vol. 23, 2005, pp. 5751-5759.
Quan et al., "Virus-Like Particle Vaccine Induces Protective Immunity against Homologous and Heterologous Strains of Influenza Virus", Journal of Virology, vol. 81. No. 7, Apr. 2007, pp. 3514-3524.
Rossman et al., "Influenza Virus M2 Ion Channel Protein is Necessary for Filamentous Virion Formation", Journal of Virology, vol. 84, No. 10, May 2010, pp. 5078-5088.
Szecsi et al., "Induction of Neutralising Antibodies by Virus-like Particles Harbouring Surface Proteins from Highly Pathogenic H5N I and H7N I Influenza Viruses", Virology Journal, 2006, 7 pages.

* cited by examiner

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
tccatgacgt tcctgacgtt                                                  20

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
tctcccagcg tgcgccat                                                    18

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
accgatgacg tcgccggtga cggcaccacg                                       30

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
tcgtcgtttt gtcgttttgt cgtt                                             24

<210> SEQ ID NO 5
<211> LENGTH: 20
<212> TYPE: DNA
<213> ORGANISM: Artificial Sequence
```

-continued

```
<220> FEATURE:
<223> OTHER INFORMATION: Synthetic Construct

<400> SEQUENCE: 5
tccatgacgt tcctgatgct                                                   20
```

CHIMERIC INFLUENZA VIRUS-LIKE PARTICLES

GOVERNMENT SUPPORT

This invention was made with United States Government support under Grant No. W81XWH-05-C-0135 and Grant No. W81XWH-05-C-0150 from the U.S. Army Medical Research and Material Command. The United States Government has certain rights in this invention.

FIELD OF THE INVENTION

The present invention relates to the field of influenza virus-like particles. In particular, chimeric influenza virus-like particles as are disclosed herein.

BACKGROUND OF THE INVENTION

Influenza A and B are the two types of influenza viruses that cause epidemic human disease (111). Influenza A viruses are further categorized into subtypes on the basis of two surface antigens: hemagglutinin (HA) and neuraminidase (NA). Influenza B viruses are not categorized into subtypes, but do under go drift whereby strains diverge over time. Since 1977, influenza A (H1N1) viruses, influenza A (H3N2) viruses, and influenza B viruses have been in global circulation. Influenza A (H1N2) viruses that probably emerged after genetic reassortment between human A (H3N2) and A (H1N1) viruses have been detected recently in many countries. Both influenza A and B viruses are further separated into groups on the basis of antigenic characteristics. New influenza virus variants result from frequent antigenic change (i.e., antigenic drift) resulting from point mutations that occur during viral replication. Influenza B viruses undergo antigenic drift less rapidly than influenza A viruses. Frequent development of antigenic variants through antigenic drift is the virologic basis for seasonal epidemics and the reason for the incorporation of at least one new strains in each year's influenza vaccine.

A person's immunity to the surface antigens, especially hemagglutinin, reduces the likelihood of infection and severity of disease if infection occurs (112). It is generally thought that antibody against one influenza virus type or subtype confers limited or no protection against another. Furthermore, it is generally accepted that antibody to one antigenic variant of influenza virus might not protect against a new antigenic variant of the same type or subtype (113). Therefore, the demonstration of cross-protection is unexpected.

Human-avian reassortant influenza viruses were responsible for the previous two influenza pandemics in 1957 and 1968. Since H2 viruses have not circulated in humans after 1968, an antigenic shift arising from an H2 reassortant virus is theoretically possible at any time. However, the recent emergence of highly pathogenic avian influenza (HPAI) viruses (H5 and H7) and the sporadic transmission of these viruses directly from birds to humans since 1997 (1-5) brings a new human pandemic threat potential in addition to the population's ever increasing susceptibility to H2 viruses. The fact that human HPAI H5N1 outbreaks have been antigenically distinct makes it all but impossible to prepare advance stockpiles of a well-matched vaccine against a pandemic threat (5, 6). While mouse H5 immunization and challenge data indicate that good cross reactivity is seen between various H5 isolates in this model (7), it is not known if similar levels of cross reactivity will be seen in humans with existing vaccine technology. Thus, there is a need for influenza vaccine platforms that may be quickly adapted to include antigens from new viral outbreaks.

The present egg-based inactivated vaccine technology is inadequate to meet the demands of an emerging pandemic due to the inability to propagate HPAI viruses in eggs and the need for enhanced biocontainment (6, 8). Reverse genetics approaches offer a means of producing low pathogenicity reassortants with the desired HA and NA makeup that can be cultured in eggs (7, 9-11); however, vaccines produced by this approach are only now entering the clinic due to previous intellectual property and regulatory issues (8). An additional concern is the apparent low level immunogenicity associated with H5 hemagglutinins evaluated in human clinical trials (12-14) which makes it clear that improved vaccines, delivery systems, and the use of adjuvants may be required to efficiently induce protection in a population that is completely H5-naïve. Thus, there is a need for an influenza vaccine platform that allows for expression of HPAI antigens in combination with adjuvants.

Influenza VLPs represent an alternative technology for generating influenza vaccines. Influenza VLPs have been produced using the influenza matrix, HA and NA proteins expressed in insect cells which are markedly immunogenic following intranasal delivery (26, 27). Indeed, VLPs in general appear well suited for the induction of mucosal and systemic immunity following intranasal delivery as has been shown for rotavirus, norovirus, and papilloma virus VLPs (28-31). Influenza VLPs have been produced in eukaryotic expression systems by expression of influenza matrix, HA and NA proteins. The influenza matrix is the driving force behind virus budding and NA is required for budded VLP release from producer cells when HA is also being expressed owing to HA's association with sialic acid at the cell surface (51). There are also data to indicate that interactions between matrix and the C-terminus of HA play a role in directing matrix to the membrane as part of the budding process (51). Influenza VLPs produced in an insect cell baculovirus expression system have proven immunogenic in animal trials and represent an important strategy for future pandemic preparedness (26, 27, 47). In addition, intranasal delivery of influenza VLPs can result in antibody titers exceeding those obtained following parenteral administration. However, preliminary data indicated that use of the matrix protein in generating influenza VLPs resulted in poor yields of VLPs which renders the matrix derived influenza VLPs a poor choice to date for an alternate form of influenza vaccine. This is consistent with more recent data showing that influenza virus particle assembly is complex and that the matrix protein is really not the driving force behind particle assembly (Chen et al J Virol. 2007 July; 81 (13):7111-23). Thus, there is a need for an influenza vaccine platform that can generate sufficient quantities of VLPs for vaccine production. In addition, there is a need for an influenza vaccine platform that can provide drift and heterosubtypic protection against influenza to rapidly provide protection against new emerging strains and subtypes before better matched vaccines can be developed and produced.

SUMMARY

The present invention meets these needs by providing various methods and compositions as disclosed herein for production and use of chimeric influenza VLPs that may be generated in sufficient quantities for vaccine production, may be delivered by a variety of means including intranasally, may be quickly adapted to novel strains of influenza virus as they arise and may include adjuvants as a part of the VLP itself as needed to enhance immunogenicity. In addition, the chimeric influenza VLPs disclosed herein can provide heterosubtypic protection against influenza. As used throughout, influenza refers generically to either or both of influenza A and B unless otherwise indicated.

In one aspect, a chimeric influenza virus-like particle has a gag polypeptide, and a neuraminidase polypeptide. In preferred embodiments the chimeric influenza virus-like particle also has a hemagglutinin polypeptide. The gag polypeptide is preferably from a retrovirus which may include murine leukemia virus, human immunodeficiency virus, Alpharetroviruses, Betaretroviruses, Gammaretroviruses, Deltaretroviruses, Deltaretroviruses and Lentiviruses. In certain embodiments, the chimeric influenza virus-like particle may include two or more hemagglutinin polypeptides from different influenza strains, preferably H1, H2, H3, H5, H7 and H9 hemagglutinins. In certain embodiments, the chimeric influenza virus-like particle may include two or more neuraminidase polypeptides from different influenza strains.

In certain embodiments, the hemagglutinin polypeptide of the chimeric influenza virus-like particle is covalently linked to an additional influenza antigen or an adjuvant polypeptide. The preferable form of covalent linkage is by splicing the gene of the influenza antigen in-frame with the hemagglutinin polypeptide gene to produce a chimeric polypeptide, preferably the influenza antigen will be linked to the N-terminus of the hemagglutinin polypeptide. In certain embodiments, the gag polypeptide of the chimeric influenza virus-like particle is covalently linked to an influenza antigen or an adjuvant. The preferable form of covalent linkage is by splicing the gene of the influenza antigen in-frame with the gag polypeptide gene to produce a chimeric polypeptide, preferably the influenza antigen will be linked to the C-terminus of the gag polypeptide. In certain embodiments, the neuraminidase polypeptide of the chimeric influenza virus-like particle is covalently linked to an influenza antigen or an adjuvant. The preferable form of covalent linkage is by splicing the gene of the influenza antigen in-frame with the neuraminidase polypeptide gene to produce a chimeric polypeptide, preferably the influenza antigen will be linked to the C-terminus of the neuraminidase polypeptide.

Preferred examples of influenza antigens that may be attached or otherwise included with the chimeric influenza virus-like particles include, without limitation, PB2, PB1, PA, nucleoprotein, Matrix (M1), BM2, NS, NS1, and NS2 or individual epitopes within the proteins or polypeptides and more preferably the influenza virus M2 epitope. For Influenza A, the preferred examples include: PB2, PB1, PA, nucleoprotein, Matrix (M1), M2, NS1, and NS2. For Influenza B, the preferred examples include: HA, NA, NP, M, PB1, PB2, PA, NS and BM2. In some embodiments, the virus-like particle may include multiple influenza antigens which may be multiple copies of the same antigen, preferably two or more, three or more, five or more or eight or more copies of the same antigen or multiple copies of different influenza antigens, preferably two or more, three or more or five or more different influenza antigens. In certain embodiments, the multiple influenza antigens may be the same antigen but from different strains of influenza.

Preferred examples of adjuvants that may be attached or otherwise included with the chimeric influenza virus-like particles may be found throughout the specification. Particularly preferred adjuvants are adjuvants that are polypeptides that may be co-expressed with or expressed as in-frame fusions with the gag polypeptide, the neuraminidase polypeptide, or the hemagglutinin polypeptide. Preferred examples of polypeptide adjuvants include flagellin and adjuvant-active fragments thereof, cytokines, colony-stimulating factors (e.g., GM-CSF, CSF, and the like); interferons; tumor necrosis factor; interleukin-2, -7, -12, and other like growth factors.

Another aspect of the chimeric influenza virus-like particles disclosed herein is expression vector systems. Such expression vector systems will typically include a first nucleotide sequence encoding a gag polypeptide and a second nucleotide sequence encoding a neuraminidase polypeptide. In preferred embodiments, the expression vector systems may include a third nucleotide sequence encoding a hemagglutinin polypeptide. Upon expression of the expression vector systems in a cellular host, the polypeptides will form a chimeric influenza virus-like particle. In certain embodiments, expression vector systems will have each nucleotide sequence in a separate vector, though preferably, some of the nucleotide sequences will be in the same vector, and most preferably, all of the nucleotide sequences will be in the same vector (i.e., the first, second, and third nucleotide sequences are in a single expression vector). In certain embodiments, each nucleotide sequence will be operably linked to its own promoter, but in some embodiments, two or more nucleotide sequences will be operably linked to the same promoter, and in some embodiments, all of the nucleotide sequences will be operably linked to the same promoter (i.e., the first, second, and third nucleotide sequences are operably linked to a single promoter). In various embodiments, the expression vector systems may include additional elements to produce the chimeric virus-like particle systems described throughout such as nucleotide sequences encoding a polypeptide adjuvant and nucleotide sequences encoding influenza antigens each of which may be expressed as separate polypeptides or included as in-frame fusions with the nucleotide sequence encoding the gag polypeptide, the neuraminidase polypeptide, the hemagglutinin polypeptide, a polypeptide adjuvant or an influenza antigen. Preferred expression vector systems are viral vector systems which may include adenoviruses, herpesviruses, poxviruses, and retroviruses and preferably baculoviruses.

Another aspect of the chimeric influenza virus-like particles disclosed herein is methods for producing a chimeric influenza virus-like particle. Preferred methods include use of the expression vector systems as disclosed herein. Preferably by providing one or more expression vectors, together which express a gag polypeptide, a neuraminidase polypeptide and in some embodiments a hemagglutinin polypeptide; introducing the one or more expression vectors into a cell; and expressing the gag polypeptide, the neuraminidase polypeptide and in some embodiments the hemagglutinin polypeptide, and to produce said chimeric influenza virus-like particle. Once the chimeric influenza virus-like particle is produced, it may be recovered from the media in which said cell is cultured. Preferred cells include insect cells and mammalian cells.

Another aspect of the chimeric influenza virus-like particles disclosed herein is methods for treating or preventing influenza comprising administering to a subject an immunogenic amount of any of the chimeric influenza virus-like particles described herein. Preferably the administering will induce a protective immunization response in the subject. Examples of methods of administration include subcutaneous delivery, intradermal delivery, subdermal delivery, transcutaneous delivery intramuscular delivery, peroral delivery, oral delivery, intranasal delivery, buccal delivery, sublingual delivery, intraperitoneal delivery, intravaginal delivery, anal delivery and intracranial delivery.

Another aspect of the chimeric influenza virus-like particles disclosed herein is pharmaceutical compositions which can include an immunogenic or therapeutic amount of any of the chimeric influenza virus-like particles describe herein. Such pharmaceutical compositions preferably will include a pharmaceutically acceptable carrier that is preferably formulated for the preferred delivery method.

In certain embodiments, the chimeric influenza virus-like particles disclosed herein induce protection against challenge from different influenza subtypes (e.g., heterosubtypic protection wherein a virus-like particle vaccine of this invention including an H1 hemagglutinin polypeptide can protect against an infection from an influenza virus containing the H3 or H5 subtype). In certain other embodiments, the chimeric influenza virus-like particles disclosed herein induce protection against virus variants or variations within a particular influenza subtype (e.g., homotypic protection wherein a virus-like particle vaccine of this invention including an H1 hemagglutinin polypeptide can protect against an infection from an influenza virus containing that H1 hemagglutinin polypeptide or a drift variant of the H1 subtype). Thus, the vaccine of this invention is able to provide robust protection against widely divergent viruses, which may be especially important in situations of pandemic influenza outbreaks.

Therefore, another aspect of the disclosed chimeric virus-like particles includes methods of using any of the virus-like particles disclosed herein to provide drift variant, homotypic and/or heterosubtypic protection against influenza by administering to a subject an immunogenic amount of a chimeric influenza virus-like particle as disclosed herein.

In certain embodiments the chimeric influenza virus-like particle vaccine will include hemagglutinin and neuraminidase polypeptides that match the currently circulating influenza virus strains, and provide homotypic protection against those strains as well as drift variants. In some embodiments, the homotypic protection will include protection against drift variants of the hemagglutinin polypeptide, e.g., variants of the H1 polypeptide. In other embodiments, the homotypic protection will include protection against drift variants of the neuraminadase polypeptide, e.g., variants of the N1 polypeptide.

In other embodiments, the chimeric influenza virus-like particle vaccine will provide heterosubtypic protection against hemagglutinin and neuraminidase strains that are not present in the chimeric VLP. For example, an H1N1 VLP provides protection against H3N2 and an H5N1 VLP provides protection against H1N1. As further examples, the VLP may provide the following types of heterosubtypic protection: protection against H2, H3, H5, H7 or H9 influenza viruses when the administered hemagglutinin polypeptide is H1; protection against H2, H5, H7 or H9 influenza viruses when the administered hemagglutinin polypeptide is H3; protection against H1, H2, H3, H7 or H9 influenza viruses when the administered hemagglutinin polypeptide is H5; protection against H1 influenza viruses when the administered hemagglutinin polypeptide is H5; protection against H3 influenza viruses when the administered hemagglutinin polypeptide is H1; and protection against N2 influenza viruses when the administered neuraminidase polypeptide is N1.

In preferred embodiments the chimeric influenza virus-like particle vaccine that includes a hemagglutinin polypeptide (e.g., H1) will provide both heterosubtypic protection against different hemagglutinin influenza virus subtypes (e.g., H2, H3, H5, H7, H9) as well as homotypic protection against H1 and drift variants of the H1 hemagglutinin. In other preferred embodiments, the virus-like particles that include a neuraminidase polypeptide (e.g., N1) will provide heterosubtypic protection against different neuraminidase influenza virus subtypes (e.g., N2) as well as homotypic protection against N1 and drift variants of N1 neuraminidase. The chimeric virus-like particles may be administered by any method available in the art, including the administration methods disclosed herein.

DETAILED DESCRIPTION OF THE PREFERRED EMBODIMENTS

Figure 1:
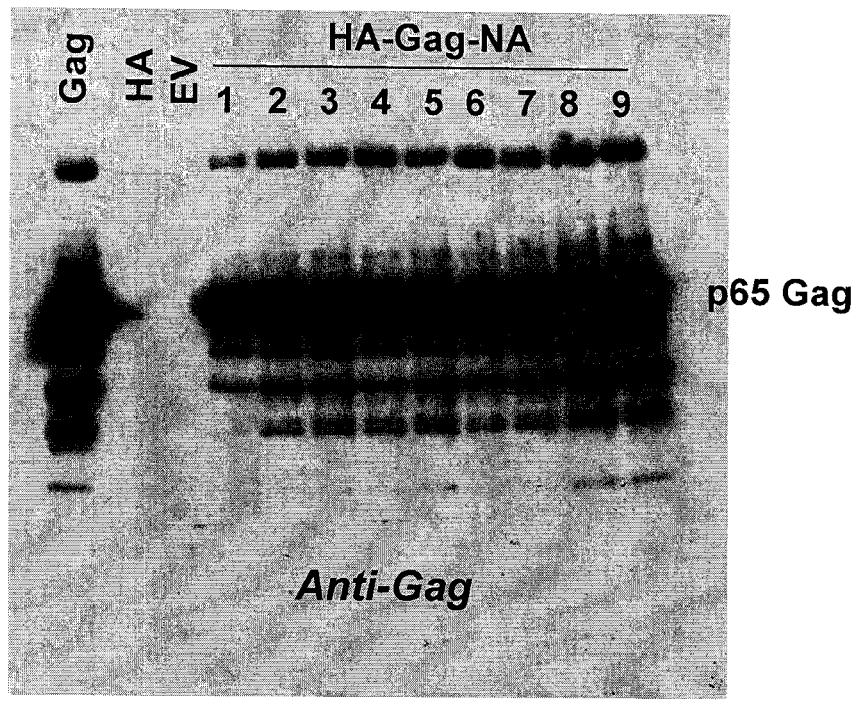
FIG. 1 shows western blots of the media from Sf9 cells infected with separate Gag, HA or control vectors and with HA-gag-NA triple vectors. (A) was probed with anti-Gag antibodies and (B) was probed with anti-HA antibodies.
Figure 1:
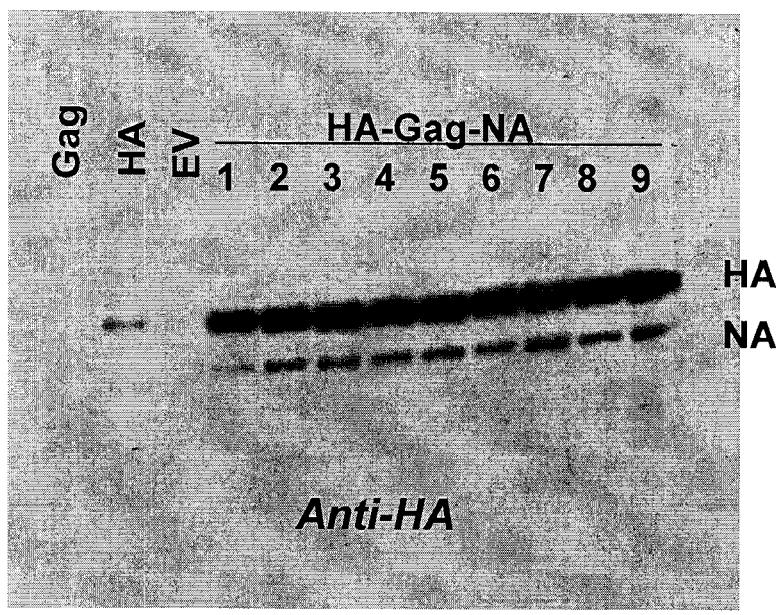
Figure 2:
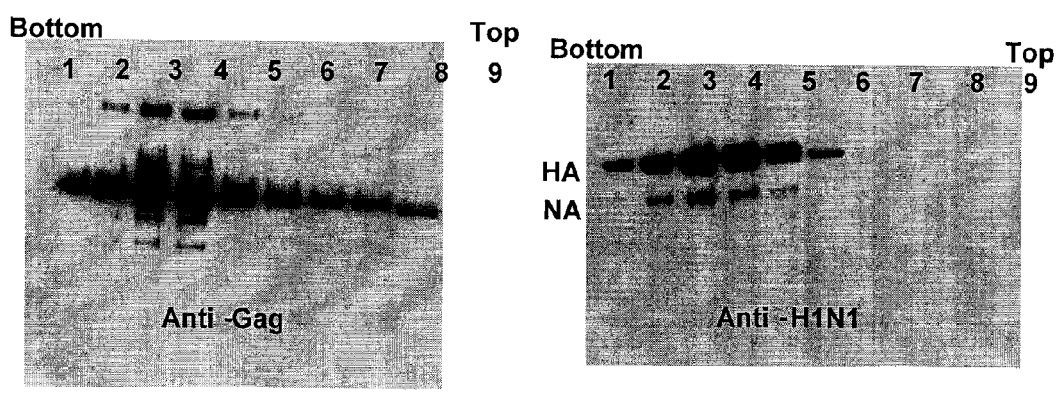
FIG. 2 shows western blots of fractions from a sucrose step gradient recentrifugation of pelleted HA-gag-NA VLPs. (A) was probed with anti-Gag antibodies and (B) was probed with anti-HA antibodies.
Figure 3:
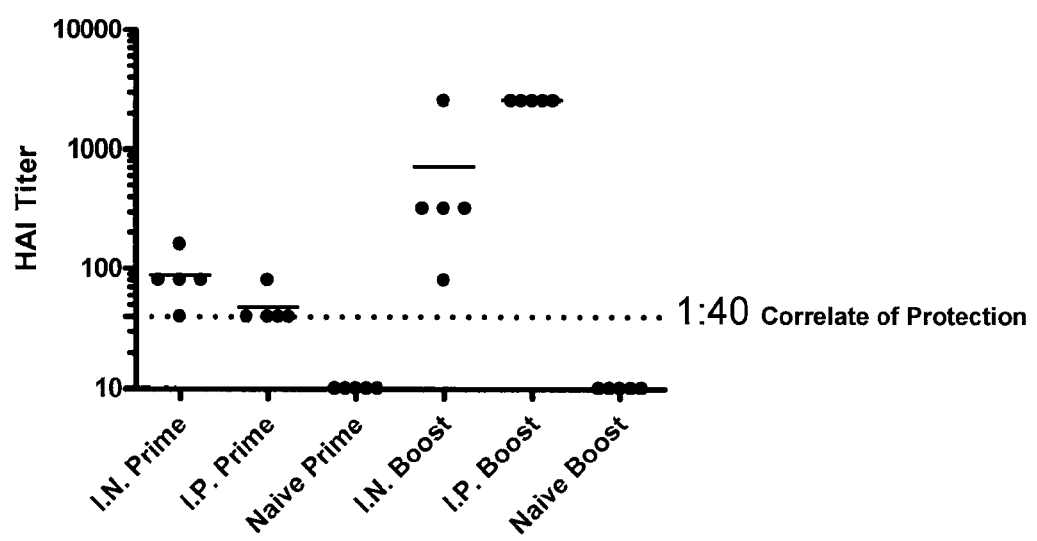
FIG. 3 shows the results of the HAI assay in which 100% of the animals in both the i.n. and i.p. immunization groups responded with protective level HAI titers (1:40, indicated by dotted line on graph) or higher following the primary immunization.
Figure 4:
FIG. 4 shows the arrangement of coding sequences in the triple expression vector for Example 1, below.

The present invention includes gag polypeptides as the basis for formation of the chimeric influenza VLPs, preferably from the murine leukemia virus (MLV). A preferred method of generating the VLPs is by expression in insect cells, preferably including coexpression of the influenza HA and NA polypeptide antigens, because of the significant yields of gag VLPs that can be obtained from a variety of retroviruses in the baculovirus expression system (23, 24, 46, 49, 52-58). Gag polypeptides inherently include C-terminal extensions in the natural retroviral assembly process in that functional gag proteins naturally have large C-terminal extensions containing retroviral protease, reverse transcriptase, and integrase activity due to ribosomal frameshifting. Production of functional gag proteins with artificial extensions has been accomplished for both RSV gag (59) and MLV gag (60). This flexibility in manipulation of the gag C-terminus provides an important site for inclusion of other polypeptides such as other antigens and immunostimulatory protein sequences such as the TLR5 agonist flagellin in influenza chimeric VLPs disclosed herein.

The production of chimeric VLPs containing a core particle from one virus and surface antigens from another is called pseudotyping. MLV gag VLPs are efficiently pseudotyped with influenza HA and NA since these proteins are concentrated within lipid raft domains (61, 62) while myristolated gag proteins also concentrate at the inner surface of lipid raft domains during the budding process (63). Recent data show that incorporation of influenza HA onto MLV gag particles in mammalian cells occurs passively at the cell membrane via concentration of both components in coincident locations (64). In addition, influenza HA molecules have been efficiently pseudotyped onto SIV VLPs as a means of markedly improving the immunogenicity of the SIV VLPs (24, 25).

In addition, with respect to influenza VLP production in a baculovirus insect cell system it can be argued that NA is not required for VLP release since terminal sialic acid residues are not found on carbohydrates in *Spodoptera frugiperda* Sf9 cells. This is consistent with data showing that influenza HA can be pseudotyped onto SIV VLPs in the absence of NA as stated above (24, 25). However, surprisingly as described in the Examples below production and release of gag-HA VLPs in baculovirus-infected insect cells requires the expression of NA. In the present expression system gag-HA co-expression in the absence of NA resulted in considerable cell clumping with a significant number of fusion events taking place. Unexpectedly, the addition of NA in the expression vector results in VLP release into the medium as well as the incorporation of an additional important antigen in the VLP vaccine.

Finally, the chimeric virus-like particles disclosed herein show an unexpected property in that they provide heterosubtypic protection against influenza as described in the Examples. Such heterosubtypic protection has only been observed with live infections or live vaccines. Thus, the disclosed chimeric virus-like particles may be used to provide heterosubtypic protection and protection against drift variants within a subtype of virus. This capacity greatly extends the utility of the disclosed virus-like particles in protecting against new variants of influenza that could lead to flu pandemics.

The practice of the disclosed methods and protocols will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

Definitions

The "Gag polypeptide" as used herein is the retrovirus derived structural polypeptide that is responsible for formation of the virus like particles described herein. In some embodiments, the gag polypeptide may be purposely mutated in order to affect certain characteristics such as the propensity to package RNA or the efficiency of particle formation and budding. One example of such a mutation would be amino acid changes that affect the ability of gag-derived VLPs to incorporate RNA. Other such amino acid changes could be made that improve or modify the efficiency of VLP budding. The genome of retroviruses codes for three major gene products: the gag gene coding for structural proteins, the pol gene coding for reverse transcriptase and associated proteolytic polypeptides, nuclease and integrase associated functions, and env whose encoded glycoprotein membrane proteins are detected on the surface of infected cells and also on the surface of mature released virus particles. The gag genes of all retroviruses have an overall structural similarity and within each group of retroviruses are conserved at the amino acid level. The gag gene gives rise to the core proteins excluding the reverse transcriptase. For MLV the Gag precursor polyprotein is $Pr65^{Gag}$ and is cleaved into four proteins whose order on the precursor is $NH_2$-p15-pp12-p30-p10-COOH. These cleavages are mediated by a viral protease and may occur before or after viral release depending upon the virus. The MLV Gag protein exists in a glycosylated and a non-glycosylated form. The glycosylated forms are cleaved from $gPr80^{Gag}$ which is synthesized from a different inframe initiation codon located upstream from the AUG codon for the non-glycosylated $Pr65^{Gag}$. Deletion mutants of MLV that do not synthesize the glycosylated Gag are still infectious and the non-glycosylated Gag can still form virus-like particles, thus raising the question over the importance of the glycosylation events. The post translational cleavage of the HIV-1 Gag precursor of $pr55^{Gag}$ by the virus coded protease yields the N-myristoylated and internally phosphorylated p17 matrix protein (p17MA), the phosphorylated p24 capsid protein (p24CA), and the nucleocapsid protein p15 (p15NC), which is further cleaved into p9 and p6.

Structurally, the prototypical Gag polyprotein is divided into three main proteins that always occur in the same order in retroviral gag genes: the matrix protein (MA) (not to be confused with influenza matrix protein M1, which shares the name matrix but is a distinct protein from MA), the capsid protein (CA), and the nucleocapsid protein (NC). Processing of the Gag polyprotein into the mature proteins is catalyzed by the retroviral encoded protease and occurs as the newly budded viral particles mature. Functionally, the Gag polyprotein is divided into three domains: the membrane binding domain, which targets the Gag polyprotein to the cellular membrane; the interaction domain which promotes Gag polymerization; and the late domain which facilitates release of nascent virions from the host cell. The form of the Gag protein that mediates assembly is the polyprotein. Thus, the assembly domains need not lie neatly within any of the cleavage products that form later. The Gag polypeptide as included herein therefore includes the important functional elements for formation and release of the VLPs. The state of the art is quite advanced regarding these important functional elements. See, e.g., Hansen et al. J. Virol 64, 5306-5316, 1990; Will et al., AIDS 5, 639-654, 1991; Wang et al. J. Virol. 72, 7950-7959, 1998; McDonnell et al., J. Mol. Biol. 279, 921-928, 1998; Schultz and Rein, J. Virol. 63, 2370-2372, 1989; Accola et al., J. Virol. 72, 2072-2078, 1998; Borsetti et al., J. Virol., 72, 9313-9317, 1998; Bowzard et al., J. Virol. 72, 9034-9044, 1998; Krishna et al., J. Virol. 72, 564-577, 1998; Wills et al., J. Virol. 68, 6605-6618, 1994; Xiang et al., J. Virol. 70, 5695-5700, 1996; Garnier et al., J. Virol. 73, 2309-2320, 1999.

As used in the VLPs of the present invention, the gag polypeptide shall at a minimum include the functional elements for formation of the VLP. The gag polypeptide may optionally include one or more additional polypeptides that may be generated by splicing the coding sequence for the one or more additional polypeptides into the gag polypeptide coding sequence. A preferred site for insertion of additional polypeptides into the gag polypeptide is the C-terminus.

Preferred retroviral sources for Gag polypeptides include murine leukemia virus, human immunodeficiency virus, Alpharetroviruses (such as the avian leucosis virus or the Rous sarcoma virus), Betaretroviruses (such as mouse mammary tumor virus, Jaagsiekte sheep retrovirus and Mason-Phizer monkey virus), Gammaretroviruses (such as murine leukemia virus, feline leukemia virus, reticuloendotheliosis virus and gibbon ape leukemia virus), Deltaretroviruses (such as human T-lymphotrophic virus and bovine leukemia virus), Epsilonretroviruses (such as walleye dermal sarcoma virus), or Lentiviruses (human immunodeficiency virus type 1, HIV-2, simian immunodeficiency virus, feline immunodeficiency virus, equine infectious anemia virus, and caprine arthritis encephalitis virus).

The "hemagglutinin polypeptide" as used herein is derived from the influenza virus protein that mediates binding of the virus to the cell to be infected. The protein is an antigenic glycoprotein found anchored to the surface of influenza viruses by a single membrane spanning domain. At least sixteen subtypes of the influenza hemagglutinin have been identified labeled H1 through H16. H1, H2, and H3, are found in human influenza viruses. Highly pathogenic avian flu viruses with H5, H7 or H9 hemagglutinins have been found to infect humans at a low rate. It has been reported that single amino acid changes in the avian virus strain's type H5 hemagglutinin have been found in human patients that alters the receptor specificity to allow the H5 hemagglutinin to significantly alter receptor specificity of avian H5N1 viruses, providing them with an ability to bind to human receptors (109 and 110). This finding explains how an H5N1 virus that normally does not infect humans can mutate and become able to efficiently infect human cells.

Hemagglutinin is a homotrimeric integral membrane polypeptide. The membrane spanning domain naturally associates with the raft-lipid domains, which allows it to associate with the gag polypeptides for incorporation into VLPs. It is shaped like a cylinder, and is approximately 135 Å long. The three identical monomers that constitute HA form a central coiled-coil and a spherical head that contains the sialic acid binding sites, which is exposed on the surface of the VLPs. HA monomers are synthesized as a single polypeptide precursor that is glycosylated and cleaved into two smaller polypeptides: the HA1 and HA2 subunits. The HA2 subunits form the trimeric coiled-coil that is anchored to the membrane and the HA1 subunits form the spherical head.

As used in the VLPs of the present invention, the hemagglutinin polypeptide shall at a minimum include the membrane anchor domain and at least one epitope from hemagglutinin. The hemagglutinin polypeptide may be derived from any influenza virus type, subtype, strain or substrain, preferably from the H1, H2, H3, H5, H7 and H9 hemagglutinins. In addition, the hemagglutinin polypeptide may be a chimera of different influenza hemagglutinins. The hemagglutinin polypeptide may optionally include one or more additional polypeptides that may be generated by splicing the coding sequence for the one or more additional polypeptides into the hemagglutinin polypeptide coding sequence. A preferred site for insertion of additional polypeptides into the hemagglutinin polypeptide is the N-terminus.

The "neuraminidase polypeptide" as used herein is derived from the influenza virus protein that mediates release of the influenza virus from the cell by cleavage of terminal sialic acid residues from glycoproteins. The neuraminidase glycoprotein is expressed on the viral surface. The neuraminidase proteins are tetrameric and share a common structure consisting of a globular head with a beta-pinwheel structure, a thin stalk region, and a small hydrophobic region that anchors the protein in the virus membrane by a single membrane spanning domain. The active site for sialic acid residue cleavage includes a pocket on the surface of each subunit formed by fifteen charged amino acids, which are conserved in all influenza A viruses. At least nine subtypes of the influenza neuraminidase have been identified labeled N1 through N9.

As used in the VLPs of the present invention, the neuraminidase polypeptide shall at a minimum include the membrane anchor domain and at least the sialic acid residue cleavage activity. The state of the art regarding functional regions is quite high. See, e.g., Varghese et al., Nature 303, 35-40, 1983; Colman et al., Nature 303, 41-44, 1983; Lentz et al., Biochem, 26, 5321-5385, 1987; Webster et al., Virol. 135, 30-42, 1984. The neuraminidase polypeptide may be derived from any influenza virus type, subtype strain or substrain, preferable from the N1 and N2 neuraminidases. In addition, the neuraminidase polypeptide may be a chimera of different influenza neuraminidase. The neuraminidase polypeptide may optionally include one or more additional polypeptides that may be generated by splicing the coding sequence for the one or more additional polypeptides into the neuraminidase polypeptide coding sequence. A preferred site for insertion of additional polypeptides into the neuraminidase polypeptide is the C-terminus.

The terms "chimeric virus-like particle" and "VLP" are used interchangeably throughout except where VLP by its context is referring to a virus-like particle that is not formed with a gag polypeptide as disclosed herein.

Preferred Methods of Making VLPs

VLPs may be readily assembled by any methods available to one of skill in the art that preferably results in the assembled VLPs including a gag polypeptide and a neuraminidase polypeptide and may further include a hemagglutinin polypeptide. In preferred embodiments, the polypeptides may be co-expressed in any available protein expression system, preferably a cell-based system that includes raft-lipid domains in the lipids such as mammalian cell expression systems and insect cell expression systems.

Numerous examples of expression of VLPs formed using a gag polypeptide have been published demonstrating the range of expression systems available for generating VLPs. Studies with several retroviruses have demonstrated that the Gag polypeptide expressed in the absence of other viral components is sufficient for VLP formation and budding at the cell surface (Wills and Craven AIDS 5, 639-654, 1991; Zhou et al., 3. Virol. 68, 2556-2569, 1994; Morikawa et al., Virology 183, 288-297, 1991; Royer et al., Virology 184, 417-422, 1991; Gheysen et al., Cell 59, 103-112, 1989; Hughes et al., Virology 193, 242-255, 1993; Yamshchikov et al., Virology 214, 50-58, 1995). Formation of VLP upon expression of the Gag precursor in insect cells using a Baculovirus vector has been demonstrated by several groups (Delchambre et al., EMBO J. 8, 2653-2660, 1989; Luo et al., Virology 179, 874-880, 1990; Royer et al., Virology 184, 417-422, 1991; Morikawa et al., Virology 183, 288-297, 1991; Zhou et al., J. Virol. 68, 2556-2569, 1994; Gheysen et al., Cell 59, 103-112, 1989; Hughes et al., Virology 193, 242-255, 1993; Yamshchikov et al., Virology 214, 50-58, 1995). These VLPs resemble immature lentivirus particles and are efficiently assembled and released by budding from the insect cell plasma membrane.

It has been reported that the amino terminal region of the Gag precursor is a targeting signal for transport to the cell surface and membrane binding which is required for virus assembly (Yu et al., J. Virol. 66, 4966-4971, 1992; an, X et al., J. Virol. 67, 6387-6394, 1993; Zhou et al., J. Virol. 68, 2556-2569, 1994; Lee and Linial J. Virol. 68, 6644-6654, 1994; Dorfman et al., J. Virol. 68, 1689-1696, 1994; Facke et al., J. Virol. 67, 4972-4980, 1993). Assembly of recombinant HIV based VLPs that contain Gag structural proteins as well as Env glycoproteins gp120 and gp41 has been reported using a vaccinia virus expression system (Haffar et al., J. Virol. 66, 4279-4287, 1992).

Recombinant expression of the polypeptides for the VLPs requires construction of an expression vector containing a polynucleotide that encodes one or more of the polypeptides. Once a polynucleotide encoding one or more of the polypeptides has been obtained, the vector for the production of the polypeptide may be produced by recombinant DNA technology using techniques well known in the art. Thus, methods for preparing a protein by expressing a polynucleotide containing any of the VLP polypeptide-encoding nucleotide sequences are described herein. Methods which are well known to those skilled in the art can be used to construct expression vectors containing the VLP polypeptide coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding a gag polypeptide, a neuraminidase polypeptide and/or a hemagglutinin polypeptide operably linked to one or more promoters.

The expression vector may be transferred to a host cell by conventional techniques and the transfected cells are then cultured by conventional techniques to produce the VLP polypeptide(s). Thus, the invention includes host cells containing a polynucleotide encoding one or more of the VLP polypeptides operably linked to a heterologous promoter. In preferred embodiments for the generation of VLPs, vectors encoding both the gag polypeptide and the neuraminidase and optionally the hemagglutinin polypeptide may be co-expressed in the host cell for generation of the VLP, as detailed below.

A variety of host-expression vector systems may be utilized to express the VLP polypeptides. Such host-expression systems represent vehicles by which the VLP polypeptides may be produced to generate VLPs preferably by co-expression. A wide range of hosts may be used in construct of appropriate expression vectors and preferred host-expression systems are those hosts that have lipid rafts suitable for assembly of the VLP. These include but are not limited to microorganisms such as bacteria (e.g., E. coli, B. subtilis) transformed with recombinant bacteriophage DNA, plasmid DNA or cosmid DNA expression vectors containing VLP polypeptide coding sequences; yeast (e.g., Saccharomyces, Pichia) transformed with recombinant yeast expression vectors containing VLP polypeptide coding sequences; insect cell systems infected with recombinant virus expression vectors (e.g., baculovirus) containing VLP polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing VLP polypeptide coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, mammalian cells and more preferably insect cells are used for the expression of the VLP polypeptides as both have membranes containing lipid rafts suitable for assembly of the VLPs. For example, mammalian cells such as Chinese hamster ovary cells (CHO), in conjunction with a vector such as the major intermediate early gene promoter element from human cytomegalovirus is an effective expression system for VLP polypeptides (Foecking et al., Gene 45:101 (1986); Cockett et al., Bio/Technology 8:2 (1990)).

In an insect system, Autographa californica nuclear polyhedrosis virus (AcNPV) may be used as a vector to express foreign genes. The virus grows in Spodoptera frugiperda cells. The VLP polypeptide coding sequence(s) may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the VLP polypeptide sequence(s) of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the VLP polypeptide(s) in infected hosts. (e.g., see Logan & Shenk, Proc. Natl. Acad. Sci. USA 81:355-359 (1984)). Specific initiation signals may also be required for efficient translation of inserted VLP polypeptide coding sequence(s). These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage or transport to the membrane) of protein products may be important for the generation of the VLP or function of a VLP polypeptide or additional polypeptide such as an adjuvant or additional antigen. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

The host cell may be co-transfected with two expression vectors described herein, the first vector encoding a gag polypeptide and the second vector encoding a neuraminidase polypeptide. In certain embodiments, a third vector encoding a hemagglutinin polypeptide may also be co-transfected or either the first or second vector may additionally express the hemagglutinin polypeptide. The two vectors may contain identical selectable markers which enable equal expression of each VLP polypeptide. Alternatively, a single vector may be used which encodes, and is capable of expressing, both the gag polypeptide and the neuraminidase polypeptide and optionally the hemagglutinin polypeptide.

Once a VLP has been produced by a host cell, it may be purified by any method known in the art for purification of a polypeptide, for example, by chromatography (e.g., ion exchange, affinity, particularly by affinity for any affinity purification tags added to the polypeptide, and sizing column chromatography), centrifugation, differential solubility, or by any other standard technique for the purification of proteins or other macromolecules. In addition, the VLP polypeptide can be fused to heterologous polypeptide sequences described herein or otherwise known in the art, to facilitate purification of the VLP. After purification, additional elements such as additional antigens or adjuvants may be physically linked to the VLP either through covalent linkage to the VLP polypeptides or by other non-covalent linkages mechanism. In preferred embodiments where the VLP polypeptides are co-expressed in a host cell that has raft-lipid domains such as mammalian cells and insect cells, the VLPs will self assemble and release allowing purification of the VLPs by any of the above methods.

Preferred Methods of Using VLPs

Formulations

A preferred use of the VLPs described herein is as a vaccine preparation. Typically, such vaccines are prepared as injectables either as liquid solutions or suspensions; solid forms suitable for solution in, or suspension in, liquid prior to injection may also be prepared. Such preparations may also be emulsified or produced as a dry powder. The active immunogenic ingredient is often mixed with excipients which are pharmaceutically acceptable and compatible with the active ingredient. Suitable excipients are, for example, water, saline, dextrose, sucrose, glycerol, ethanol, or the like, and combinations thereof. In addition, if desired, the vaccine may contain auxiliary substances such as wetting or emulsifying agents, pH buffering agents, or adjuvants which enhance the effectiveness of the vaccines.

Vaccines may be conventionally administered parenterally, by injection, for example, either subcutaneously, intradermally, subdermally or intramuscularly. Additional formulations which are suitable for other modes of administration include suppositories and, in some cases, oral, intranasal, buccal, sublingual, intraperitoneal, intravaginal, anal and intracranial formulations. For suppositories, traditional binders and carriers may include, for example, polyalkalene glycols or triglycerides; such suppositories may be formed from mixtures containing the active ingredient in the range of 0.5% to 10%, preferably 1-2%. In certain embodiments, a low melting wax, such as a mixture of fatty acid glycerides or cocoa butter is first melted and the VLPs described herein are dispersed homogeneously, for example, by stirring. The molten homogeneous mixture is then poured into conveniently sized molds, allowed to cool, and to solidify.

Formulations suitable for intranasal delivery include liquids and dry powders. Formulations include such normally employed excipients as, for example, pharmaceutical grades of mannitol, lactose, sucrose, trehalose, and chitosan. Mucosadhesive agents such as chitosan can be used in either liquid or powder formulations to delay mucocilliary clearance of intranasally-administered formulations. Sugars such as mannitol and sucrose can be used as stability agents in liquid formulations and as stability and bulking agents in dry powder formulations. In addition, adjuvants such as monophosphoryl lipid A (MPL) and, by way of example but not limitation, double stranded poly (I:C), poly inosinic acid, CpG-containing oligonucleotides, imiquimod, cholera toxin and its derivative, heat labile enterotoxin and its derivative and many of the adjuvants listed throughout the specification, can be used in both liquid and dry powder formulations as an immunostimulatory adjuvant.

Formulations suitable for oral delivery include liquids, solids, semi-solids, gels, tablets, capsules, lozenges, and the like. Formulations suitable for oral delivery include tablets, lozenges, capsules, gels, liquids, food products, beverages, nutraceuticals, and the like. Formulations include such normally employed excipients as, for example, pharmaceutical grades of mannitol, lactose, starch, magnesium stearate, sodium saccharine, cellulose, magnesium carbonate, and the like. Other VLP vaccine compositions may take the form of solutions, suspensions, pills, sustained release formulations or powders and contain 10-95% of active ingredient, preferably 25-70%. For oral formulations, cholera toxin is an interesting formulation partner (and also a possible conjugation partner).

The VLP vaccines when formulated for vaginal administration may be in the form of pessaries, tampons, creams, gels, pastes, foams or sprays. Any of the foregoing formulations may contain agents in addition to VLPs, such as carriers, known in the art to be appropriate.

In some embodiments, the VLP vaccine may be formulated for systemic or localized delivery. Such formulations are well known in the art. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Systemic and localized routes of administration include, e.g., intradermal, topical application, intravenous, intramuscular, etc.

The VLPs may be formulated into the vaccine including neutral or salt-based formulations. Pharmaceutically acceptable salts include acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines may be administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 µg to 2000 µg (even though higher amounts in the 1-10 mg range are contemplated), such as in the range from about 0.5 µg to 1000 µg, preferably in the range from 1 µg to 500 µg and especially in the range from about 10 µg to 100 µg. Suitable regimens for initial administration and booster shots are also variable but are typified by an initial administration followed by subsequent inoculations or other administrations.

The manner of application may be varied widely. Any of the conventional methods for administration of a vaccine are applicable. These include oral application on a solid physiologically acceptable base or in a physiologically acceptable dispersion, parenterally, by injection or the like. The dosage of the vaccine will depend on the route of administration and will vary according to the age of the person to be vaccinated and the formulation of the antigen.

Some of the vaccine formulations will be sufficiently immunogenic as a vaccine by themselves, but for some of the others the immune response will be enhanced if the vaccine further comprises an adjuvant substance.

Delivery agents that improve mucoadhesion can also be used to improve delivery and immunogenicity especially for intranasal, oral or lung based delivery formulations. One such compound, chitosan, the N-deacetylated form of chitin, is used in many pharmaceutical formulations (32). It is an attractive mucoadhesive agent for intranasal vaccine delivery due to its ability to delay mucociliary clearance and allow more time for mucosal antigen uptake and processing (33, 34). In addition, it can transiently open tight junctions which may enhance transepithelial transport of antigen to the NALT. In a recent human trial, a trivalent inactivated influenza vaccine administered intranasally with chitosan but without any additional adjuvant yielded seroconversion and HI titers that were only marginally lower than those obtained following intramuscular inoculation (33).

Chitosan can also be formulated with adjuvants that function well intranasally such as the genetically detoxified *E. coli* heat-labile enterotoxin mutant LTK63. This adds an immunostimulatory effect on top of the delivery and adhesion benefits imparted by chitosan resulting in enhanced mucosal and systemic responses (35).

Finally, it should be noted that chitosan formulations can also be prepared in a dry powder format that has been shown to improve vaccine stability and result in a further delay in mucociliary clearance over liquid formulations (42). This was seen in a recent human clinical trial involving an intranasal dry powder diphtheria toxoid vaccine formulated with chitosan in which the intranasal route was as effective as the traditional intramuscular route with the added benefit of secretory IgA responses (43). The vaccine was also very well tolerated. Intranasal dry powdered vaccines for anthrax containing chitosan and MPL induce stronger responses in rabbits than intramuscular inoculation and are also protective against aerosol spore challenge (44).

Insofar as traditional influenza vaccines are parenterally administered and largely induce (or boost) systemic IgG responses protecting the lower respiratory tract, new vaccine approaches that induce mucosal responses are more desirable as they can restrict virus growth in both the upper and lower respiratory tracts and are likely the best vaccine approach for individual protection and reduction of transmission (15). Vaccine approaches that offer promise in this direction include the use of attenuated, cold-adapted viruses (8) as well as intranasal formulations of non-replicating antigens such as virus-like particles, recombinant HA antigens, and replication-defective viral vectors.

In addition to providing protection in both the upper and lower respiratory tracts, intranasal vaccines avoid the complications of needle inoculations and provide a means of inducing both mucosal and systemic humoral and cellular responses via interaction of particulate and/or soluble antigens with nasopharyngeal-associated lymphoid tissues (NALT) (16-19). The intranasal route has been historically less effective than parenteral inoculation, but the use of VLPs, novel delivery formulations, and adjuvants are beginning to change the paradigm. Indeed, influenza vaccines containing functional hemagglutinin molecules may be especially well suited for intranasal delivery due to the abundance of sialic acid-containing receptors in the nasal mucosa resulting in the potential for enhanced HA antigen binding and reduced mucociliary clearance.

With respect to influenza, protective immune responses including heterosubtypic protection have been reported following intranasal vaccine delivery in experiments where parallel parenteral administrations were less immunogenic and did not induce heterosubtypic protection (20-22). Moreover, inactivated influenza has been shown to be an effective adjuvant for systemic and mucosal humoral and cellular responses when admixed with a simian immunodeficiency virus (SIV) VLP vaccine administered intranasally (23). This adjuvant effect was attributed to the ability of inactivated influenza virions to aggregate with the VLPs and lead to enhanced binding to mucosal surfaces. A similar adjuvant effect was also seen when influenza HA was directly incorporated into SIV VLPs which led to enhanced binding to and activation of dendritic cells (DC) (24, 25).

Adjuvants

Various methods of achieving adjuvant effect for vaccines are known and may be used in conjunction with the VLPs disclosed herein. General principles and methods are detailed in "*The Theory and Practical Application of Adjuvants*", 1995, Duncan E. S. Stewart-Tull (ed.), John Wiley & Sons Ltd, ISBN 0-471-95170-6, and also in "*Vaccines: New Generation Immunological Adjuvants*", 1995, Gregoriadis G et al. (eds.), Plenum Press, New York, ISBN 0-306-45283-9, both of which are hereby incorporated by reference herein.

In some embodiments, a VLP vaccine comprises the VLP in admixture with at least one adjuvant, at a weight-based ratio of from about 10:1 to about $10^{10}$:1 VLP:ajuvant, e.g., from about 10:1 to about 100:1, from about 100:1 to about $10^3$:1, from about $10^3$:1 to about $10^4$:1, from about $10^4$:1 to about $10^5$:1, from about $10^5$:1 to about $10^6$:1, from about $10^6$:1 to about $10^7$:1, from about $10^7$:1 to about $10^8$:1, from about $10^8$:1 to about $10^9$:1, or from about $10^9$:1 to about $10^{10}$:1 VLP:adjuvant. One of skill in the art can readily determine the appropriate ratio through information regarding the adjuvant and routine experimentation to determine optimal ratios. One of skill in the art can readily determine the appropriate ratio through information regarding the adjuvant and routine experimentation to determine optimal ratios. Admixtures of VLPs and adjuvants as disclosed herein may include any form of combination available to one of skill in the art including, without limitation, mixture of separate VLPs and adjuvants in the same solution, covalently linked VLPs and adjuvants, ionically linked VLPs and adjuvants, hydrophobically linked VLPs and adjuvants (including being embedded partially or fully in the VLP membrane), hydrophilically linked VLPs and adjuvants, and any combination of the foregoing.

Preferred examples of adjuvants are polypeptide adjuvants that may be readily added to the VLPs described herein by co-expression with the VLP polypeptides or fusion with the VLP polypeptides to produce chimeric polypeptides. Bacterial flagellin, the major protein constituent of flagella, is a preferred adjuvant which has received increasing attention as an adjuvant protein because of its recognition by the innate immune system by the toll-like receptor TLR5 (65). Flagellin signaling through TLR5 has effects on both innate and adaptive immune functions by inducing DC maturation and migration as well as activation of macrophages, neutrophils, and intestinal epithelial cells resulting in production of proinflammatory mediators (66-72).

TLR5 recognizes a conserved structure within flagellin monomers that is unique to this protein and is required for flagellar function, precluding its mutation in response to immunological pressure (73). The receptor is sensitive to a 100 fM concentration but does not recognize intact filaments. Flagellar disassembly into monomers is required for binding and stimulation.

As an adjuvant, flagellin has potent activity for induction of protective responses for heterologous antigens administered either parenterally or intranasally (66, 74-77) and adjuvant effects for DNA vaccines have also been reported (78). A Th2 bias is observed when flagellin is employed which would be appropriate for a respiratory virus such as influenza but no evidence for IgE induction in mice or monkeys has been observed. In addition, no local or systemic inflammatory responses have been noted following intranasal or systemic administration in monkeys (74). The Th2 character of responses elicited following use of flagellin is somewhat surprising since flagellin signals through TLR5 in a MyD88-dependent manner and all other MyD88-dependent signals through TLRs have been shown to result in a Th1 bias (67, 79). Importantly, pre-existing antibodies to flagellin have no appreciable effect on adjuvant efficacy (74) making it attractive as a multi-use adjuvant.

A common theme in many recent intranasal vaccine trials is the use of adjuvants and/or delivery systems to improve vaccine efficacy. In one such study an influenza H3 vaccine containing a genetically detoxified *E. coli* heat-labile enterotoxin adjuvant (LT R192G) resulted in heterosubtypic protection against H5 challenge but only following intranasal delivery. Protection was based on the induction of cross neutralizing antibodies and demonstrated important implications for the intranasal route in development of new influenza vaccines (22).

Cytokines, colony-stimulating factors (e.g., GM-CSF, CSF, and the like); tumor necrosis factor; interleukin-2, -7, -12, and other like growth factors, may also be used as adjuvants and are also preferred as they may be readily included in the VLP vaccine by admixing or fusion with the VLP polypeptides.

In some embodiments, the VLP vaccine compositions disclosed herein may include other adjuvants that act through a Toll-like receptor such as a nucleic acid TLR9 ligand comprising a CpG oligonucleotide; an imidazoquinoline TLR7 ligand; a substituted guanine TLR7/8 ligand; other TLR7 ligands such as Loxoribine, 7-deazadeoxyguanosine, 7-thia-8-oxodeoxyguanosine, double stranded poly (I:C), poly-inosinic acid, Imiquimod (R-837), and Resiquimod (R-848); or a TLR4 agonist such as MPL® or synthetic derivatives.

Certain adjuvants facilitate uptake of the vaccine molecules by APCs, such as dendritic cells, and activate these. Non-limiting examples are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM matrix); a particle; DDA; aluminum adjuvants; DNA adjuvants; MPL; and an encapsulating adjuvant.

Additional examples of adjuvants include agents such as aluminum salts such as hydroxide or phosphate (alum), commonly used as 0.05 to 0.1 percent solution in buffered saline (see, e.g., Nicklas (1992) Res. Immunol. 143:489-493), admixture with synthetic polymers of sugars (e.g. Carbopol®) used as 0.25 percent solution, aggregation of the protein in the vaccine by heat treatment with temperatures ranging between 70° to 101° C. for 30 second to 2 minute periods respectively and also aggregation by means of cross-linking agents are possible. Aggregation by reactivation with pepsin treated antibodies (Fab fragments) to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Admixture with oils such as squalene and IFA is also preferred.

DDA (dimethyldioctadecylammonium bromide) is an interesting candidate for an adjuvant, but also Freund's complete and incomplete adjuvants as well as *quillaja* saponins such as QuilA and QS21 are interesting. Further possibilities include poly[di(earboxylatophenoxy)phosphazene (PCPP) derivatives of lipopolysaccharides such as monophosphoryl lipid A (MPL®), muramyl dipeptide (MDP) and threonyl muramyl dipeptide (tMDP). The lipopolysaccharide based adjuvants are preferred for producing a predominantly Th1-type response including, for example, a combination of monophosphoryl lipid A, preferably 3-de-O-acylated monophosphoryl lipid A, together with an aluminum salt. MPL® adjuvants are available from GlaxoSmithKline (see, for example, U.S. Pat. Nos. 4,436,727; 4,877,611; 4,866,034 and 4,912,094, each of which is incorporated by reference in their entirety with particular reference to their lipopolysaccharides related teachings).

Liposome formulations are also known to confer adjuvant effects, and therefore liposome adjuvants are preferred examples in conjunction with the VLPs.

Immunostimulating complex matrix type (ISCOM® matrix) adjuvants are preferred choices for use with the VLP vaccines, especially since it has been shown that this type of adjuvants are capable of up-regulating MHC Class II expression by APCs. An ISCOM matrix consists of (optionally fractionated) saponins (triterpenoids) from *Quillaja saponaria*, cholesterol, and phospholipid. When admixed with the immunogenic protein such as in the VPLs, the resulting particulate formulation is what is known as an ISCOM particle where the saponin may constitute 60-70% w/w, the cholesterol and phospholipid 10-15% w/w, and the protein 10-15% w/w. Details relating to composition and use of immunostimulating complexes can for example be found in the above-mentioned text-books dealing with adjuvants, but also Morein B et al., 1995, Clin. Immunother. 3: 461-475 as well as Barr I G and Mitchell G F, 1996, Immunol. and Cell Biol. 74: 8-25 (both incorporated by reference herein) provide useful instructions for the preparation of complete immunostimulating complexes.

The saponins, whether or not in the form of ISCOMs, that may be used in the adjuvant combinations with the VLP vaccines disclosed herein include those derived from the bark of *Quillaja Saponaria* Molina, termed Quil A, and fractions thereof, described in U.S. Pat. No. 5,057,540 (which is incorporated by reference herein in its entirety with particular reference to the fractions of Quil A and methods of isolation and use thereof) and "Saponins as vaccine adjuvants", Kensil, C. R., Crit. Rev Ther Drug Carrier Syst, 1996, 12 (1-2):1-55; and EP 0 362 279 B1. Particularly preferred fractions of Quil A are QS21, QS7, and QS17.

β-Escin is another preferred hemolytic saponins for use in the adjuvant compositions of the VLP vaccines described herein. Escin is described in the Merck index (12th ed: entry 3737) as a mixture of saponins occurring in the seed of the horse chestnut tree, Lat: *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin have been purified and shown to be biologically active (Yoshikawa M, et al. (Chem Pharm Bull (Tokyo) 1996 August; 44 (8):1454-1464)). β-escin is also known as aescin.

Another preferred hemolytic saponin for use with the VLP vaccines is Digitonin. Digitonin is described in the Merck index (12.sup.th Edition, entry 3204) as a saponin, being derived from the seeds of *Digitalis purpurea* and purified according to the procedure described Gisvold et al., J. Am. Pharm. Assoc., 1934, 23, 664; and Ruhenstroth-Bauer, Physiol. Chem., 1955, 301, 621. Its use is described as being a clinical reagent for cholesterol determination.

Another interesting (and thus, preferred) possibility of achieving adjuvant effect is to employ the technique described in Gosselin et al., 1992 (which is hereby incorporated by reference herein). In brief, the presentation of a relevant antigen such as the VLP polypeptides or additional antigens described herein can be enhanced by conjugating the antigen to antibodies (or antigen binding antibody fragments) against the $F_c$ receptors on monocytes/macrophages. Especially conjugates between antigen and anti-$F_c$RI have been demonstrated to enhance immunogenicity for the purposes of vaccination. The antibody may be conjugated to the VLP after generation or as a part of the generation including by expressing as a fusion to any one of the VLP polypeptides.

Other possibilities involve the use of the targeting and immune modulating substances (i.e. cytokines). In addition, synthetic inducers of cytokines such as poly I:C may also be used.

Suitable mycobacterial derivatives may be selected from the group consisting of muramyl dipeptide, complete Freund's adjuvant, and a diester of trehalose such as TDM and TDE.

Examples of suitable immune targeting adjuvants include CD40 ligand and CD40 antibodies or specifically binding fragments thereof (cf. the discussion above), mannose, a Fab fragment, and CTLA-4.

Examples of suitable polymer adjuvants include a carbohydrate such as dextran, PEG, starch, mannan, and mannose; a plastic polymer; and latex such as latex beads.

Yet another interesting way of modulating an immune response is to include the immunogen (optionally together with adjuvants and pharmaceutically acceptable carriers and vehicles) in a "virtual lymph node" (VLN) (a proprietary medical device developed by ImmunoTherapy, Inc., 360 Lexington Avenue, New York, N.Y. 10017-6501). The VLN (a thin tubular device) mimics the structure and function of a lymph node. Insertion of a VLN under the skin creates a site of sterile inflammation with an upsurge of cytokines and chemokines. T- and B-cells as well as APCs rapidly respond to the danger signals, home to the inflamed site and accumulate inside the porous matrix of the VLN. It has been shown that the necessary antigen dose required to mount an immune response to an antigen is reduced when using the VLN and that immune protection conferred by vaccination using a VLN surpassed conventional immunization using Ribi as an adjuvant. The technology is described briefly in Gelber C et al., 1998, "Elicitation of Robust Cellular and Humoral Immune Responses to Small Amounts of Immunogens Using a Novel Medical Device Designated the Virtual Lymph Node", in: "From the Laboratory to the Clinic, Book of Abstracts, Oct. 12-15, 1998, Seascape Resort, Aptos, Calif."

Oligonucleotides may be used as adjuvants in conjunction with the VLP vaccines and preferably contain two or more dinucleotide CpG motifs separated by at least three or more preferably at least six or more nucleotides. CpG-containing oligonucleotides (in which the CpG dinucleotide is unmethylated) induce a predominantly Th1 response. Such oligonucleotides are well known and are described, for example, in WO 96/02555, WO 99/33488 and U.S. Pat. Nos. 6,008,200 and 5,856,462, each of which is hereby incorporated by reference in their entirety with particular reference to methods of making and using CpG oligonucleotides as adjuvants.

Such oligonucleotide adjuvants may be deoxynucleotides. In a preferred embodiment the nucleotide backbone in the oligonucleotide is phosphorodithioate, or more preferably a phosphorothioate bond, although phosphodiester and other nucleotide backbones such as PNA may be used with the VLP vaccines including oligonucleotides with mixed backbone linkages. Methods for producing phosphorothioate oligonucleotides or phosphorodithioate are described in U.S. Pat. Nos. 5,666,153, 5,278,302 and WO95/26204, each of which are hereby incorporated by reference in their entirety with particular reference to the phosphorothioate and phosphorodithioate teachings.

Examples of preferred oligonucleotides have the following sequences. The sequences preferably contain phosphorothioate modified nucleotide backbones.

```
(SEQ ID NO: 1) OLIGO 1:
TCC ATG ACG TTC CTG ACG TT (CpG 1826)

(SEQ ID NO: 2) OLIGO 2:
TCT CCC AGC GTG CGC CAT (CpG 1758)

(SEQ ID NO: 3) OLIGO 3:
ACC GAT GAC GTC GCC GGT GAC GGC ACC ACG (SEQ ID NO: 4) OLIGO 4:
TCG TCG TTT TGT CGT TTT GTC GTT (CpG 2006)

(SEQ ID NO: 5) OLIGO 5:
TCC ATG ACG TTC CTG ATG CT (CpG 1668)
```

Alternative preferred CpG oligonucleotides include the above sequences with inconsequential deletions or additions thereto. The CpG oligonucleotides as adjuvants may be synthesized by any method known in the art (e.g., EP 468520). Preferably, such oligonucleotides may be synthesized utilizing an automated synthesizer. Such oligonucleotide adjuvants may be between 10-50 bases in length. Another adjuvant system involves the combination of a CpG-containing oligonucleotide and a saponin derivative particularly the combination of CpG and QS21 is disclosed in WO 00/09159.

Many single or multiphase emulsion systems have been described. One of skill in the art may readily adapt such emulsion systems for use with VLPs so that the emulsion does not disrupt the VLP's structure. Oil in water emulsion adjuvants per se have been suggested to be useful as adjuvant compositions (EPO 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424,067; EP 0 480 981 B).

The oil emulsion adjuvants for use with the VLP vaccines described herein may be natural or synthetic, and may be mineral or organic. Examples of mineral and organic oils will be readily apparent to the man skilled in the art.

In order for any oil in water composition to be suitable for human administration, the oil phase of the emulsion system preferably comprises a metabolizable oil. The meaning of the term metabolizable oil is well known in the art. Metabolizable can be defined as "being capable of being transformed by metabolism" (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts (such as peanut oil), seeds, and grains are common sources of vegetable oils. Synthetic oils may also be used with the VLP vaccines and can include commercially available oils such as NEOBEE® and others. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use with the VLP vaccines disclosed herein. Squalene is a metabolizable oil virtue of the fact that it is an intermediate in the biosynthesis of cholesterol (Merck index, 10th Edition, entry no. 8619).

Particularly preferred oil emulsions are oil in water emulsions, and in particular squalene in water emulsions.

In addition, the most preferred oil emulsion adjuvants for use in the VLP vaccines comprise an antioxidant, which is preferably the oil α-tocopherol (vitamin E, EP 0 382 271 B1).

WO 95/17210 and WO 99/11241 disclose emulsion adjuvants based on squalene, α-tocopherol, and TWEEN 80, optionally formulated with the immunostimulants QS21 and/or 3D-MPL. WO 99/12565 discloses an improvement to these squalene emulsions with the addition of a sterol into the oil phase. Additionally, a triglyceride, such as tricaprylin ($C_{27}H_{50}O_6$), may be added to the oil phase in order to stabilize the emulsion (WO 98/56414).

The size of the oil droplets found within the stable oil in water emulsion are preferably less than 1 micron, may be in the range of substantially 30-600 nm, preferably substantially around 30-500 nm in diameter, and most preferably substantially 150-500 nm in diameter, and in particular about 150 nm in diameter as measured by photon correlation spectroscopy. In this regard, 80% of the oil droplets by number should be within the preferred ranges, more preferably more than 90% and most preferably more than 95% of the oil droplets by number are within the defined size ranges. The amounts of the components present in the oil emulsions are conventionally in the range of from 2 to 10% oil, such as squalene; and when present, from 2 to 10% alpha tocopherol; and from 0.3 to 3% surfactant, such as polyoxyethylene sorbitan monooleate. Preferably the ratio of oil:alpha tocopherol is equal or less than 1 as this provides a more stable emulsion. Span 85 may also be present at a level of about 1%. In some cases it may be advantageous that the VLP vaccines disclosed herein will further contain a stabilizer.

The method of producing oil in water emulsions is well known to the man skilled in the art. Commonly, the method comprises the mixing the oil phase with a surfactant such as a PBS/TWEEN80® solution, followed by homogenization using a homogenizer, it would be clear to a man skilled in the art that a method comprising passing the mixture twice through a syringe needle would be suitable for homogenizing small volumes of liquid. Equally, the emulsification process in microfluidizer (M110S microfluidics machine, maximum of 50 passes, for a period of 2 minutes at maximum pressure input of 6 bar (output pressure of about 850 bar)) could be adapted by the man skilled in the art to produce smaller or larger volumes of emulsion. This adaptation could be achieved by routine experimentation comprising the measurement of the resultant emulsion until a preparation was achieved with oil droplets of the required diameter.

The VLP vaccine preparations disclosed herein may be used to protect or treat a mammal or bird susceptible to, or suffering from viral influenza, by means of administering said vaccine by intranasal, intramuscular, intraperitoneal, intradermal, transdermal, intravenous, or subcutaneous administration. Methods of systemic administration of the vaccine preparations may include conventional syringes and needles, or devices designed for ballistic delivery of solid vaccines (WO 99/27961), or needleless pressure liquid jet device (U.S. Pat. Nos. 4,596,556; 5,993,412), or transdermal patches (WO 97/48440; WO 98/28037). The VLP vaccines may also be applied to the skin (transdermal or transcutaneous delivery WO 98/20734; WO 98/28037). The VLP vaccines disclosed herein therefore includes a delivery device for systemic administration, pre-filled with the VLP vaccine or adjuvant compositions. Accordingly there is provided a method for inducing an immune response in an individual preferably mammal or bird, comprising the administration of a vaccine comprising any of the VLP compositions described herein and optionally including an adjuvant and/or a carrier, to the individual, wherein the vaccine is administered via the parenteral or systemic route.

Preferably the VLP vaccine preparations disclosed herein may be used to protect or treat a mammal or bird susceptible to, or suffering from viral influenza, by means of administering said vaccine via a mucosal route, such as the oral/alimentary or nasal route. Alternative mucosal routes are intravaginal and intra-rectal. The preferred mucosal route of administration is via the nasal route, termed intranasal vaccination. Methods of intranasal vaccination are well known in the art, including the administration of a droplet, spray, or dry powdered form of the vaccine into the nasopharynx of the individual to be immunized. Nebulized or aerosolized vaccine formulations are therefore preferred forms of the VLP vaccines disclosed herein. Enteric formulations such as gastro resistant capsules and granules for oral administration, suppositories for rectal or vaginal administration are also formulations of the VLP vaccines disclosed herein.

The preferred VLP vaccine compositions disclosed herein, represent a class of mucosal vaccines suitable for application in humans to replace systemic vaccination by mucosal vaccination.

The VLP vaccines may also be administered via the oral route. In such cases the pharmaceutically acceptable excipient may also include alkaline buffers, or enteric capsules or microgranules. The VLP vaccines may also be administered by the vaginal route. In such cases, the pharmaceutically acceptable excipients may also include emulsifiers, polymers such as CARBOPOL®, and other known stabilizers of vaginal creams and suppositories. The VLP vaccines may also be administered by the rectal route. In such cases the excipients may also include waxes and polymers known in the art for forming rectal suppositories.

Alternatively the VLP vaccines formulations may be combined with vaccines vehicles composed of chitosan (as described above) or other polycationic polymers, polylactide and polylactide-coglycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM.

Additional illustrative adjuvants for use in the pharmaceutical and vaccine compositions using VLPs as described herein include SAF (Chiron, Calif., United States), MF-59 (Chiron, see, e.g., Granoff et al. (1997) Infect Immun. 65 (5):1710-1715), the SBAS series of adjuvants (e.g., SB-AS2 (SmithKline Beecham adjuvant system #2; an oil-in-water emulsion containing MPL and QS21); SBAS-4 (SmithKline Beecham adjuvant system #4; contains alum and MPL), available from SmithKline Beecham, Rixensart, Belgium), Detox (Enhanzyn®) (GlaxoSmithKline), RC-512, RC-522, RC-527, RC-529, RC-544, and RC-560 (GlaxoSmithKline) and other aminoalkyl glucosaminide 4-phosphates (AGPs), such as those described in pending U.S. patent application Ser. Nos. 08/853,826 and 09/074,720, the disclosures of which are incorporated herein by reference in their entireties.

Other examples of adjuvants include, but are not limited to, Hunter's TiterMax® adjuvants (CytRx Corp., Norcross, Ga.); Gerbu adjuvants (Gerbu Biotechnik GmbH, Gaiberg, Germany); nitrocellulose (Nilsson and Larsson (1992) Res. Immunol. 143:553-557); alum (e.g., aluminum hydroxide, aluminum phosphate) emulsion based formulations including mineral oil, non-mineral oil, water-in-oil or oil-in-water emulsions, such as the Seppic ISA series of Montamide adjuvants (e.g., ISA-51, ISA-57, ISA-720, ISA-151, etc.; Seppic, Paris, France); and PROVAX® (IDEC Pharmaceuticals); OM-174 (a glucosamine disaccharide related to lipid A); *Leishmania* elongation factor; non-ionic block copolymers that form micelles such as CRL 1005; and Syntex Adjuvant Formulation. See, e.g., O'Hagan et al. (2001) Biomol Eng. 18 (3):69-85; and "Vaccine Adjuvants: Preparation Methods and Research Protocols" D. O'Hagan, ed. (2000) Humana Press.

Other preferred adjuvants include adjuvant molecules of the general formula

$$HO(CH_2CH_2O)_n\text{—}A\text{—}R, \quad (I)$$

wherein, n is 1-50, A is a bond or —C(O)—, R is $C_{1-50}$ alkyl or Phenyl $C_{1-50}$ alkyl.

One embodiment of the VLP vaccine formulations described herein include a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{1-2}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index (12th edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described above.

Further examples of suitable pharmaceutically acceptable excipients for use with the VLP vaccines disclosed herein include water, phosphate buffered saline, isotonic buffer solutions.

Additional Influenza Antigens

The VLPs disclosed herein may include additional antigens from influenza to increase the immunogenicity with respect to particular strains of influenza and/or across multiple strains of influenza.

A preferred additional influenza antigen is the M2 polypeptide (also called BM2 in influenza B). The M2 polypeptide of influenza virus is a small 97 amino acid class III integral membrane protein encoded by RNA segment 7 (matrix segment) following a splicing event (80, 81). Very little M2 exists on virus particles but it can be found more abundantly on infected cells. M2 serves as a proton-selective ion channel that is necessary for viral entry (82, 83). It is minimally immunogenic during infection or conventional vaccination, explaining its conservation, but when presented in an alternative format it is more immunogenic and protective (84-86). This is consistent with observations that passive transfer of an M2 monoclonal antibody in vivo accelerates viral clearance and results in protection (87). When the M2 external domain epitope is linked to HBV core particles as a fusion protein it is protective in mice via both parenteral and intranasal inoculation and is most immunogenic when three tandem copies are fused to the N-terminus of the core protein (88-90). This is consistent with other carrier-hapten data showing that increased epitope density increases immunogenicity (91).

For intranasal delivery of an M2 vaccine an adjuvant is required to achieve good protection and good results have been achieved with LTR192G (88, 90) and CTA1-DD (89). The peptide can also be chemically conjugated to a carrier such as KLH, or the outer membrane protein complex of *N. meningitides*, or human papilloma virus VLPs and is protective as a vaccine in mice and other animals (92, 93).

Insofar as the M2 protein is highly conserved it is not completely without sequence divergence. The M2 ectodomain epitopes of common strains A/PR/8/34 (H1N1) and A/Aichi/68 (H3N2) were shown to be immunologically cross reactive with all other modern sequenced human strains except for A/Hong Kong/156/97 (H5N1) (92). Examination of influenza database sequences also shows similar divergence in the M2 sequence of other more recent pathogenic H5N1 human isolates such as A/Vietnam/1203/04. This finding demonstrates that a successful H5-specific pandemic vaccine incorporating M2 epitopes will need to reflect the M2 sequences that are unique to the pathogenic avian strains rather than M2 sequences currently circulating in human H1 and H3 isolates.

Additional proteins from influenza virus (other than HA, NA and M2) may be included in the VLP vaccine either by co-expression or via linkage of all or part of the additional antigen to the gag or HA polypeptides. These additional antigens include PB2, PB1, PA, nucleoprotein, matrix (M1), BM2, NS, NS1, and NS2. For Influenza A, the preferred examples include: PB2, PB1, PA, nucleoprotein, Matrix (M1), M2, NS1, and NS2. For Influenza B, the preferred examples include: HA, NA, NP, M, PB1, PB2, PA, NS and BM2. These latter antigens are not generally targets of neutralizing antibody responses but may contain important epitopes recognized by T cells. T cell responses induced by a VLP vaccine to such epitopes may prove beneficial in boosting protective immunity.

PREFERRED METHODS

EXAMPLE 1

Production of a Chimeric Influenza VLP

The MLV gag coding sequence was obtained by PCR from plasmid pAMS (ATCC) containing the entire Moloney murine leukemia virus amphotropic proviral sequence. The gag coding sequence was inserted into pFastBac1 (Invitrogen) behind the polyhedron promoter and the resulting plasmid was transformed into DH10Bac competent cells for recombination into the baculovirus genome. High molecular weight bacmid DNA was then purified and transfected into Sf9 cells for generation of a gag-expressing recombinant baculovirus. Two other recombinant baculoviruses encoding the hemagglutinin and neuraminidase, respectively, of A/PR/8/34 (H1N1) were produced in a similar fashion after RT-PCR cloning of the HA and NA coding sequences from virus RNA. Finally, a single baculovirus vector encoding all three products (HA-gag-NA) was produced by combining the HA, gag, and NA expression units (polyhedron promoter—coding sequence—polyA site) from individual pFastBac1 plasmids into a single pFastBac1 vector. For initial analysis, recombinant baculoviruses encoding gag or HA or gag-HA-NA were infected into Sf9 cells in 6 well plates at an MOI of >1. Three days following infection, medium supernatants were clarified of debris then pelleted at 100,000×g through a 20% sucrose cushion. Pellets were analyzed by Western blot analysis using gag and H1N1-specific antisera (See FIGS. 1A and B).

The left three lanes on each blot in FIGS. 1A and B, respectively, show the results of infecting Sf9 cells with separate gag or HA or control (EV=empty vector) baculoviruses prior to harvesting the medium. As expected, infection with a gag-only baculovirus results in significant amounts of gag antigen in the high molecular weight medium fraction due to VLP budding (FIG. 1A, lane "Gag"). In contrast, infection with an HA only baculovirus, results in little HA released into the medium on its own (FIG. 1B, lane "HA"). However, infection of Sf9 cells with a HA-gag-NA triple vector results in significant amounts of both gag and HA appearing in the 100,000×g fraction (lanes 1-9, FIGS. 1A and B) showing that gag expression can pull HA out of the cell.

The FIGS. 2A and B show the results of recentrifugation of pelleted HA-gag-NA VLPs on a 20-60% sucrose step gradient followed by Western blot analysis of individual gradient fractions. Both gag and HA peak in the same fraction demonstrating coincident banding at a density of approximately 1.16 g/ml which indicates that the gag and HA were in VLPs.

EXAMPLE 2

Intranasal Delivery of Chimeric Influenza VLPs

The HA-gag-NA VLPs were prepared from the medium of Sf9 cells infected with a triple expression baculovirus vector encoding MLV gag and the HA and NA products of influenza virus A/PR/8/34. Medium was harvested when cell viability dropped below 10% and was clarified of cell debris by centrifugation at 2000 rpm for 15 minutes. Forty ml of clarified medium (5 ml per MLA-80 ultracentrifuge tube) was layered over 1 ml 20% sucrose cushions in tris-buffered saline (TBS), pH 7.4, then centrifuged at 45,000 rpm for 2 hours at 10° C. in a MLA-80 rotor. The pelleted material was resuspended in TBS and layered over 20-60% sucrose step gradients and centrifuged at 36,000 rpm for 2 hours at 10° C. in a MLA-80 rotor. Gradients were fractionated into 0.5 ml fractions and assayed for the presence of p65 gag on SDS-PAGE gels. Pooled fractions containing VLPs (approximately 3 ml from two gradients) were concentrated and buffer exchanged into TBS using a centrifuge microconcentrator. VLP yields were estimated by analysis of a small aliquot by SDS-PAGE.

Two groups of female Balb/c mice (5 per immunization group) were vaccinated with approximately 5-10 μg of VLP (based on quantitation of gag) via the intranasal and intraperitoneal routes, respectively. Each animal received two such immunizations spaced 1 month apart. Intranasal immunizations were made of 5 μl VLP suspension, 4.5 μl 10% chitosan in water and 0.5 μl of 10 mg/ml monophosphoryl lipid A (MPL) in 90% ethanol. The 10 μl immunization doses were evenly divided between the two nares. Intraperitoneal immunizations consisted of 5 μl VLP suspension, 2 μl 10/mg/ml MPL in 90% ethanol and 93 μl saline (total 100 μl per dose). Sera samples were collected from each mouse two weeks following each immunization and were assayed for hemagglutination inhibition (HAI) activity using a standard assay widely employed in the field of influenza vaccine research. Sera samples from 5 naïve control mice were also processed in parallel to serve as a negative control. The FIG. 3 shows the results of the HAI assay in which 100% of the animals in both the i.n. and i.p. immunization groups responded with protective level HAI titers (1:40, indicated by dotted line on graph) or higher following the primary immunization. Immune responses markedly increased further following receipt of the booster immunization. Control animals exhibited no HAI activity (titer<1:10).

This example demonstrates the efficacy of intranasal delivery of the VLPs vaccines disclosed herein.

EXAMPLE 3

Production, Characterization and Immunogenicity Testing of HA-gag-NA VLPs

As described in the Example 1, individual baculoviruses expressing MLV gag and the HA and NA products of A/PR/8/34 have been produced. In addition a triple expression recombinant baculovirus encoding all three products has also been constructed and sucrose density gradient centrifugation of pelleted medium supernatants from infected insect cells showed coincident banding of gag and HA as detected by Western blotting indicating that VLPs with HA had formed. The arrangement of coding sequences in the triple expression vector is shown in FIG. 4 in which the HA, gag, and NA coding elements are arranged in a head-to-tail fashion, each with its own promoter (Pr) and polyadenylation sequence (pA). Combining all coding sequences into a single baculovirus avoids the need to perform co-infections with separate viruses and the associated difficulties of achieving consistent multiplicities of infection of three separate viruses.

Prior studies examining the possibility of VLP formation using only gag and HA were less successful. Baculovirus expression of HA in Sf9 cells in the absence of NA resulted in marked cell to cell clumping and a significant number of fusion events. This was not observed when NA is co-expressed with HA. Even though Sf9 insect cells lack significant amounts of sialic acid (103), surprisingly, NA co-expression enhanced VLP release from baculovirus-infected Sf9 cells.

Hemagglutination Assay:

Sucrose density gradient fractions of banded VLPs will be screened for hemagglutination activity using a standard assay employing chicken or guinea pig RBCs to demonstrate that the HA antigenic activity that bands coincidentally with MLV gag is functional HA. Influenza virus A/PR/8/34 grown in embryonated eggs will also be banded on sucrose gradients and subjected to hemagglutination assays as a positive control.

Size Exclusion Chromatography:

Sucrose density gradient purified VLPs will be subjected to size exclusion chromatography using Sepharose CL-4B and fractions will be monitored for MLV gag and HA by Western blot. VLPs will elute in the void volume and will contain MLV gag, HA and NA. A/PR/8/34 virus will be chromatographed as a control.

Electron Microscopy:

VLP samples from sucrose gradients will be treated with 2% glutaraldehyde, adsorbed onto EM grids, negatively stained with sodium phosphotungstate and examined by electron microscopy.

Immunogenicity:

VLP immunogenicity will be evaluated in female Balb/c mice using intranasal chitosan/MPL formulations similar to the anthrax protective antigen (PA) formulation described in reference (44) and in Example 2 above. VLPs will be purified by pelleting VLP-containing culture medium through 20% sucrose cushions at 100,000×g for 1 hour after which they will be resuspended in Tris-buffered saline and banded on 20-60% sucrose density gradients. VLP-containing fractions will be identified by Western blot or hemagglutination assay and pooled. VLPs samples will be dialyzed into PBS and concentrated using centrifuge microconcentrators or by centrifugation at 100,000×g.

For immunization, liquid formulations (15 μl) containing 40 μg chitosan, 20 μg VLP (based on gag), and 5 μg MPL will be divided between the two nostrils for a single immunization. Animals will be lightly anesthetized with isoflurane prior to intranasal dosing at 0 and 4 weeks. VLPs will also be formulated in PBS with MPL or cholera toxin for intraperitoneal inoculation as a positive control. Additional positive control animals will receive intramuscular inoculations with chemically inactivated MDCK cell-grown A/PR/8/34 virus. Systemic IgG responses will be monitored by hemagglutination inhibition (HAI) assay and ELISA. For ELISA, the antigen source will be A/PR/8/34 virus grown in eggs to avoid detection of immune responses to serum products that may be contaminating the VLPs produced in insect cells. For animals that will not be kept alive for viral challenge, broncoaveolar lavage samples will be collected 10-14 days following the final immunization for measurement of influenza-specific IgA responses by ELISA.

Typical immunization experiments in this Example 2 and the Examples below will employ a minimum of eight mice per group this will provide a reasonable probability of achieving statistical significance as shown using Student's unpaired t-test. Immunizations will typically entail primary and booster inoculations spaced four weeks apart with blood sampling occurring 10-14 days following each immunization. As stated above, broncoaveolar lavage samples will be collected from sacrificed animals for IgA determination.

A challenge will also be performed in which mice immunized as above will be intranasally challenged with approximately 10 $LD_{50}$ of mouse adapted A/PR/8/34 virus in order to confirm the protective nature of induced responses. Half of the animals in each group (8) will be monitored for weight loss and sacrificed when 25% weight loss is observed. The remaining 8 animals in each group will be sacrificed on day four post challenge and nasal and lung tissues will be collected and snap frozen. Tissues will later be thawed, homogenized in cold PBS, clarified and titered for virus by plaque assay in MDCK cells. Table 1 shows a summary of the animal studies for this Example 2.

TABLE 1

Example 3: Animal studies

| Study | | # of mice |
|---|---|---|
| 1 | A/PR/8/34 virus titration in mice | 48 |
| 2 | Initial VLP Immunogenicity | |
| | Group 1: Neg. control | 8 |
| | Group 2: VLP i.n. chitosan/MPL | 8 |
| | Group 3: VLP parenteral - pos. control | 8 |
| | Group 4: Intact flu - pos. control | 8 |
| 3 | Initial VLP Challenge Trial | |
| | Group 1: Neg. control | 16 |
| | Group 2: VLP i.n. chitosan/MPL | 16 |
| | Group 3: VLP parenteral - pos. control | 16 |
| | Group 4: Intact flu - pos. control | 16 |

EXAMPLE 4

Production and Immunogenicity Testing of Enhanced VLPs

This Example 4 will demonstrate the enhancements of the VLPs for improved immunogenicity and protection by incorporation of the TLR5 agonist flagellin to boost the strength of adaptive immune responses and by incorporation of the M2 ectodomain epitope to improve protection against drifted variants and heterosubtypes.

Adjuvant Effects Due to Flagellin Incorporation:

The flagellin coding sequence was recently cloned from *S. typhimurium* genomic DNA and inserted at the 3' end of the gag coding sequence just 5' to the termination codon. The flagellin coding sequence will also be inserted at the N-terminus of the A/PR/8/34 HA coding sequence using a PstI site located at the boundary between the signal peptide and mature coding sequences. Insertions at this location in HA lead to proper expression of chimeric HA molecules with expected molecular weight increases as demonstrated by SDS PAGE. Flagellin-modified gag and HA coding sequences will be used to generate triple baculovirus recombinants (HA-gag-NA) as described in Example 1. Recombinant baculoviruses encoding VLPs with flagellin-modified gag or flagellin-modified HA will be produced and used to generate VLPs for immunogenicity testing versus basic VLPs lacking flagellin sequences. As stated in Example 3, all immunization experiments will employ primary and booster inoculations spaced four weeks apart. Immunological readouts will be via HAI and ELISA assays as described above, examining both systemic IgG and mucosal IgA responses.

Because the HA and gag insertion sites for flagellin incorporation are outside and inside the VLP, respectively, different degrees of adjuvant effects will be observed. Flagellin insertion at the N-terminus of HA will result in easy access of flagellin to TLR5 receptors on cells in the epithelial mucosa. In contrast, the gag site of insertion will result in different access. VLP binding to cells and internalization via the normal influenza virus entry pathway will result in the deposition of the gag-flagellin product within the cell. This will result in differential TLR5-mediated adjuvant effects between the gag-flagellin and the HA-flagellin constructs. Since the ability of VLPs to bind to and enter mucosal epithelial cells may in itself have an effect on immunogenicity, we will perform VLP immunogenicity studies of flagellin-modified and normal VLPs with and without TPCK-trypsin treatment. HA cleavage of trypsin-treated VLPs will be confirmed by Western blot prior to the initiation of immunogenicity studies examining the importance of VLP entry. In addition, the ability of trypsin-treated VLPs to fuse with and enter cells will be examined by in vitro fluorescence microscopy studies employing VLPs containing a green fluorescent protein (GFP)-modified gag product. It has already been shown that MLV gag can be modified at its C-terminus with GFP without abrogation of its budding activity (60).

The use of subfragments of the flagellin coding sequence to maximize gag budding activity by eliminating much of the non-TLR5 binding regions of flagellin will also be tested. Recent mapping of the TLR5 recognition sites within the flagellin monomer will facilitate this effort (73).

Enhanced Protection Via M2 Epitope Insertion:

The M2 ectodomain epitope coding sequence has been generated by PCR and a single copy of this sequence was inserted into the PstI site bordering the signal peptide and mature coding sequences of PR/8/34 HA. Western blot analysis of the expression of this chimera in insect cells showed a chimeric HA-M2 product of the expected size that reacted with both HA-specific and M2-specific antibodies (not shown). Constructs containing 2 and 3 tandem copies of the M2 element in this same location are in progress. Triple expression baculovirus recombinants encoding HA(M2)-gag-NA VLPs (with 1, 2 or 3 M2 copies) will be produced for immunogenicity and challenge protection comparisons versus basic VLPs. Mice will be immunized with intranasal chitosan/MPL formulations as described above and immune responses will be monitored via HAI and ELISA assays. ELISA assays will employ either whole virus or the M2 ectodomain peptide to separately monitor responses to HA/NA and M2. In addition, immunized animals will be challenged with either A/PR/8/34 (H1N1) or A/KH/68 (H3N2) to monitor homotypic and heterosubtypic protection, respectively. Weight loss/survival and virus titrations in MDCK cells post challenge will be performed as described above. Table 2 below shows a summary of the animal studies proposed for Specific Aim 2.

As stated above, a recombinant HA molecule containing a single copy of the M2 ectodomain sequence at the N-terminus has been successfully expressed. Normal HA expression in Sf9 cells in the absence of NA results in significant cell clumping and fusion. Similarly, expression of the M2-modified HA construct resulted in an identical pattern of cell clumping and fusion indicating that the HA co-expressed with M2 was functional. In addition, a recombinant HA containing a 500 by coding sequence insertion at the N-terminus has also been successfully expressed, so expressing other constructs that may be much larger will encounter few problems, if any, including, without limitation, future flagellin coding sequence insertion and multiple M2 insertions at this location.

TABLE 2

Example 4: Animal studies

| Study | | # of mice |
|---|---|---|
| 1 | Flagellin-enhanced VLP Immunogenicity test | |
| | Group 1: Neg. control | 8 |
| | Group 2: VLP w/gag-flagellin | 8 |
| | Group 3: VLP w/HA-flagellin | 8 |
| | Group 4: Basic VLP | 8 |
| | Group 5: VLP w/gag-flagellin + trypsin treatment | 8 |
| | Group 6: VLP w/HA-flagellin + trypsin treatment | 8 |
| | Group 7: Basic VLP + trypsin treatment | 8 |
| 2 | Initial VLP Challenge Trial | |
| | Group 1: Neg. control | 16 |
| | Group 2: Basic VLP | 16 |
| | Group 3: VLP w/one copy of M2 | 16 |
| | Group 4: VLP w/two copies of M2 | 16 |
| | Group 5: VLP w/three copies of M2 | 16 |

EXAMPLE 5

Immunogenicity of H5-Containing VLPs and Measurement of Protective Efficacy

The HA and NA genes of A/Vietnam/1203/04 (H5N1) and A/Indonesia/5/05 (H5N1) have been obtained for production of H5N1 VLPs and subsequent H5N1 immunogenicity studies. Triple baculovirus expression vectors encoding HA-gag-NA from both H5N1 strains have been produced and characterized as described in Example 3. Vietnam and Indonesia H5N1 VLPs encoded by the two triple baculovirus expression vectors were purified by banding on 20-60% sucrose density gradients and fractions containing VLPs were identified by SDS-PAGE, Western blot, and hemagglutination assays. All three assays identified the same peak fractions as containing the bulk of the H5N1 VLPs. For immunization of mice, peak fractions were pooled, diluted three-fold with Tris-buffered saline and VLPs were concentrated by sedimentation at 100,000×g and resuspended in PBS.

Figure 8:
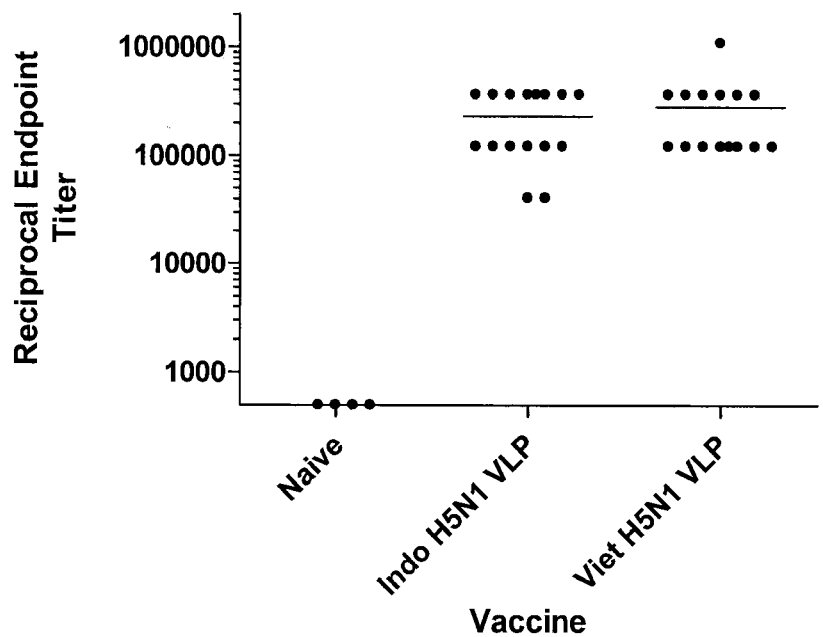
FIG. 8 shows the specificity of sera from immunized mice for a commercially-obtained recombinant H5 Vietnam HA molecule used in the ELISA assay.

To examine H5N1 VLP immunogenicity, two groups of 15 and 16 mice were immunized by intramuscular inoculation with A/Vietnam 1203/04 VLPs and A/Indonesia/5/05 VLPs, respectively. Inoculations contained VLPs (approximately 10 µg in PBS) supplemented with 10 µg MPL. Animals received two such immunization spaced four weeks apart and serum samples were collected 14 days following the second immunization. FIG. 8 shows the specificity of sera from immunized mice for a commercially-obtained recombinant H5 Vietnam HA molecule used in an ELISA assay. Strong H5-specific reactivity was observed in animals immunized with either H5N1 VLP preparation but no H5 reactivity was observed in naïve control mice.

Figure 9:
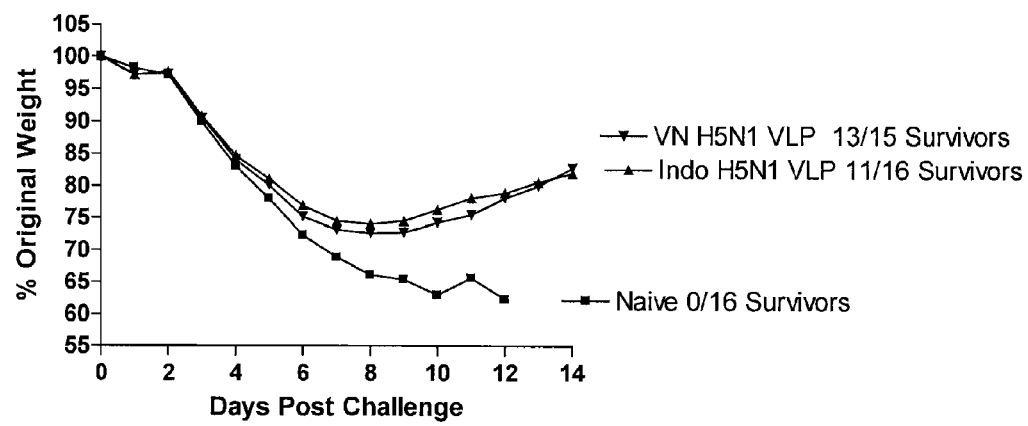
FIG. 9 shows the weight loss and survival data from Indonesia H5N1 VLP-vaccinated, Vietnam H5N1 VLP-vaccinated, and naïve mice following H1N1 challenge.

All H5N1-immunized mice and 16 naïve control mice were challenged with 10 LD50 of A/PR/8/34 (H1N1) virus to determine if the H5-specific responses could induce protection against a heterosubtypic H1N1 challenge. FIG. 9 shows the weight loss data post-challenge in this study in which there were 0/16 survivors in the naïve group, 11/16 survivors in Indonesia H5N1 immunization group, and 13/15 survivors in the Vietnam H5N1 immunization group. On day 5 post-challenge H5-immunized mice began to show decreased weight loss relative to naïve mice and began recovering lost weight on day 9. Naïve mice all continued to lose weight until all animals had died. These data demonstrate that chimeric H5N1 VLPs can induce a partial heterosubtypic protection (77% survivors) against an H1N1 challenge showing the breadth of protection that can be obtained using this influenza vaccine technology platform.

EXAMPLE 6

Evaluation of Dry Powder Intranasal Formulations in Rabbits for Both H1 and H5 Enhanced VLP Vaccines Dry powder formulations of intranasal vaccines have shown enhanced efficacy versus liquid formulations (42-44). Rabbits will be utilized for dry powder formulation and immunization studies because mice are too small for intranasal dry powder delivery and good efficacy of intranasal dry powder vaccines has been demonstrated in the rabbit model.

An important consideration is the extent to which influenza VLPs produced in this program can be lyophilized and formulated as a dry powder without jeopardizing VLP structure and immunogenicity. The process for dry powder vaccine formulation involves lyophilization of vaccine and MPL in the presence of an excess of mannitol to serve as a bulking agent, after which chitosan is added via mixing with a glass mortar and pestle (44). The final mixture is passed through a 250 micron sieve prior to loading into Valois Monopowder intranasal delivery devices. While mannitol has been employed as a preferable bulking agent, it has also been shown to contribute to the stability of phospholipid:cholesterol liposomes during lyophilization (104). The addition of polyvinylpyrrolidone (PVP) can further enhance liposome integrity and minimize loss of contents during lyophilization (104). Since the HA-gag-NA VLPs described here are composed of a phosholipid:cholesterol membranes via budding through lipid raft domains, it is likely that their integrity during lyophilization will also be enhanced by the presence of mannitol and PVP.

Further evidence for the ability to successfully lyophilize enveloped VLPs comes from data showing that live influenza virus and other enveloped viruses can be lyophilized and stored with minimal loss of infectivity (105-107). The most recent data demonstrate successful lyophilization and storage of cold-adapted live attenuated influenza virus strains in the presence of phosphate buffered saline, SPG (sucrose, mono and dibasic potassium phosphate, and potassium glutamate) and Casitone (casein hydrolysate). Casein hydrolysate could also serve as an acceptable bulking agent for intranasal powder delivery since it is hypoallergenic compared to intact casein and can be safely fed to children with cow milk allergy (108).

Before immunization of animals, various lyophilization formulations will be tested to optimize structural and antigenic integrity of VLPs for dry powder formulations. Formulations containing mannitol, mannitol+PVP, and SPG+Casitone with variations in the concentrations of stabilizers will be tested. Analysis of VLP integrity following lyophilization will involve rehydration of VLPs followed by sucrose density gradient banding. Gradient fractions will be analyzed by Western blot for the presence of HA and gag and integrity of the HA will be monitored by HA assay. The formulation providing the most consistent VLP integrity compared to nonlyophilized controls will be employed for subsequent dry powder vaccine formulation.

The efficacy of liquid and dry powder intranasal formulations of enhanced H1 VLPs containing chitosan and MPL in rabbits will be compared. Two groups of six rabbits each will be immunized with enhanced H1 VLPs using liquid and dry powder formulations, respectively. Two additional groups of six rabbits will serve as positive (i.m. VLP+MPL) and negative (intranasal chitosan only) controls. Serum samples collected following primary and booster immunizations will be examined for influenza reactivity via ELISA and HA assay. If responses appear insufficient, a second booster immunization will be administered. Evidence for protection against homotypic H1 or heterosubtypic (H3N2) challenge will be obtained by passive transfer of immune rabbit sera to mice (1 ml intraperitoneal injection of pooled group rabbit sera per mouse) one hour prior to challenge. Each mouse challenge group will contain sixteen animals, eight of which will be monitored for weight loss and eight will be sacrificed on day 4 for virus titrations in lungs. A summary table for Example 6 animal studies is below (Table 4).

If data from the H1 rabbit immunization trial show evidence of intranasal dry powder vaccine efficacy, a confirmatory intranasal dry powder experiment will be performed with enhanced H5 VLP vaccines in rabbits as well. To this end, two groups of six rabbits each will be immunized via intranasal dry powder delivery with enhanced H5/Vietnam VLPs and H5/Indonesia VLPs, respectively. All animals will receive primary and booster immunizations on days 0 and 28. A negative control group will receive a chitosan only vaccine. Rabbit sera collected fourteen days following the second immunization will be analyzed for neutralization activity for A/Vietnam/1203/04. If necessary, a second booster immunization will be administered. Rabbits will be bled out and pooled group sera will be used for passive immunization of mice and challenge with A/Vietnam/1203/04 using 16 mice per group (eight mice monitored for weight loss/survival and eight mice sacrificed on day 4 for virus titrations in MDCK cells). Data from this experiment will determine whether or not intranasal dry powder immunizations using enhanced H5 VLP vaccines will induce homotypic and drift variant protection.

TABLE 4

Example 6: Animal studies

| Study | | |
|---|---|---|
| 1a | H1 VLP - Rabbit Immunization | # of rabbits |
| | Group 1: H1 enhanced VLP - intranasal liquid | 6 |
| | Group 2: H1 enhanced VLP - intranasal dry | 6 |
| | Group 3: H1 enhanced VLP - parenteral control | 6 |
| | Group 4: Neg. control | 6 |
| 1b | Passive transfer of rabbit sera to mice for challenge | # of mice |
| | Group 1: H1 enhanced VLP - intranasal liquid | 32 |
| | Group 2: H1 enhanced VLP - intranasal dry | 32 |
| | Group 3: H1 enhanced VLP - parenteral control | 32 |
| | Group 4: Neg. control | 32 |
| | | 16 |
| 2a | H5 VLP - Rabbit Immunization | # of rabbits |
| | Group 1: H5 Vietnam enhanced VLP | 6 |
| | Group 2: H5 Indonesia enhanced VLP | 6 |
| | Group 3: Neg. control | 6 |
| 2b | Passive transfer of rabbit sera to mice for challenge | # of mice |
| | Group 1: H5 Vietnam enhanced VLP | 32 |
| | Group 2: H5 Indonesia enhanced VLP | 32 |
| | Group 3: Neg. control | 32 |

EXAMPLE 7

Figure 5:
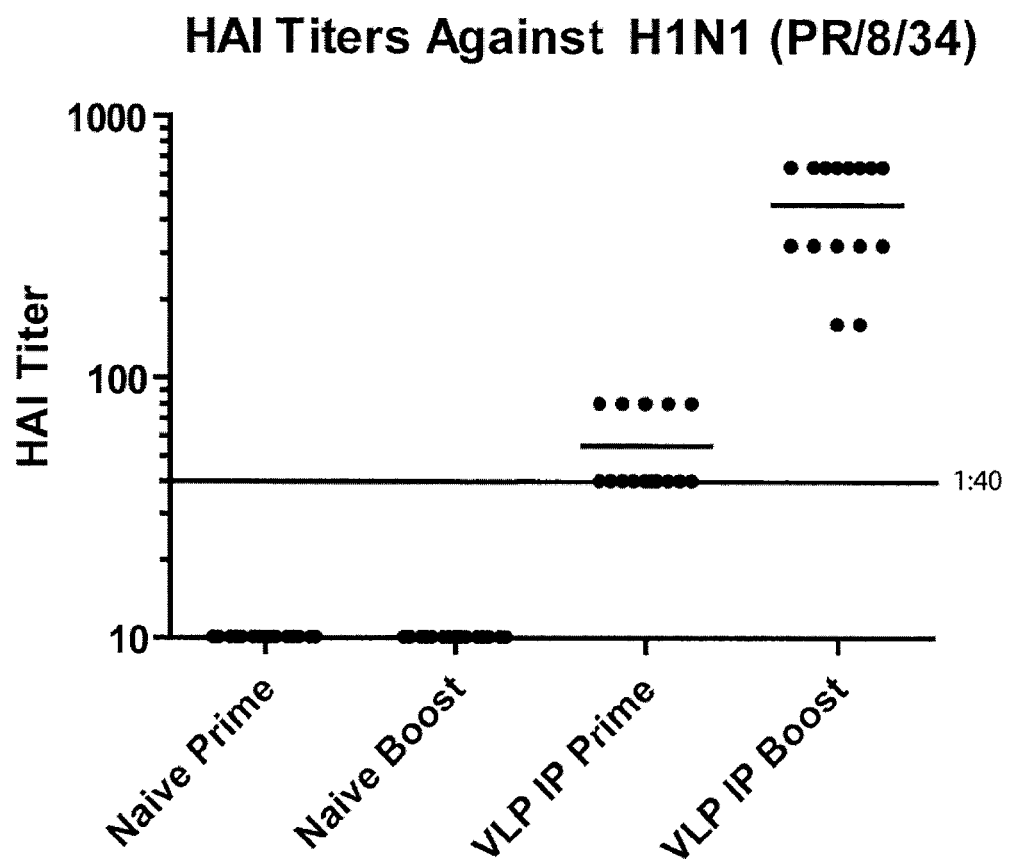
FIG. 5 shows immunogenicity of gag-HA-NA VLPs (H1N1) following primary and booster immunizations via i.p. inoculation.

Basic VLPs Induce Homotypic and Heterosubtypic Protection Against Lethal Challenge in Mice An immunization and challenge study employing basic H1N1 VLPs (gag+HA(H1)+NA(N1)) for immunization and mouse adapted H1N1 (A/PR/8/34) and H3N2 swarm (A/HK/68+A/Mem/85) challenge viruses was conducted. FIG. 5 shows hemagglutination inhibition (HAI) titers in mice following primary and booster immunization with 5 µg H1N1 VLP and 20 µg monophosphoryl lipid A (MPL) in saline. I.P. immunizations were spaced 4 weeks apart and serum samples were collected 2 weeks following each immunization. Sera samples were treated with receptor-destroying enzyme (RDE) and assayed for HAI activity using a standard assay employing fresh chick RBCs. All 16 VLP-immunized animals developed strong HAI titers against egg-grown H1N1 (A/PR/8/34). As expected, no HAI activity was observed against H3N2 swarm (A/HK/68+A/Mem/85). Naïve control animals also exhibited no HAI reactivity against either H1N1 or H3N2 viruses.

Figure 6:
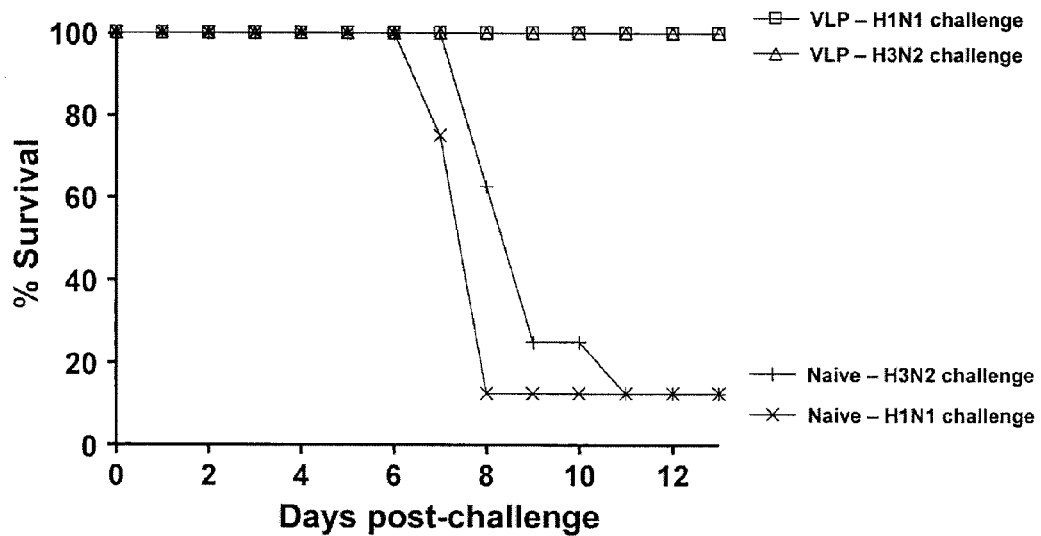
FIG. 6 shows survival data from VLP-vaccinated and naïve mice following H1N1 and H3N2 swarm challenge.

Five weeks following the booster immunization, vaccinated and naïve animals (16 mice per group) were divided into two 8-mouse cohorts and challenged with 10 $LD_{50}$ of mouse-adapted H1N1 (A/PR/8/34) and H3N2 swarm (A/HK/68+A/Mem/85), respectively. Survival data are shown in FIG. 6. As expected from the HAI titers, 100% survival was observed in VLP-vaccinated mice challenged with the H1N1 virus. Unexpectedly, 100% survival was also observed in VLP-vaccinated animals challenged with H3N2 swarm despite the absence of any detectable H3 HAI activity (other humoral and cellular assays have yet to be performed). All naive animals challenged with H1N1 or H3N2 exhibited marked morbidity and 7 of 8 animals in each naïve challenge group either died or were sacrificed after being found moribund.

Figure 7:
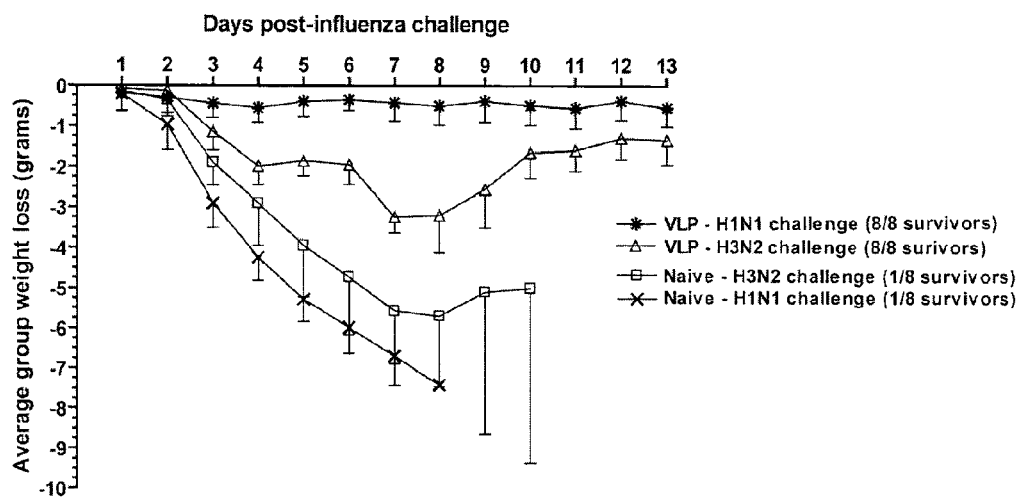
FIG. 7 shows weight loss data from VLP-vaccinated and naïve mice following H1N1 and H3N2 swarm challenge.

Weight loss data following the challenge are plotted in FIG. 7 and reveal different patterns of morbidity in the various groups. Animals were examined daily for signs of illness and weight loss. As expected, VLP-vaccinated animals challenged with H1N1 showed little if any weight loss and exhibited no signs of illness. On the other hand, VLP-vaccinated animals challenged with H3N2 swarm exhibited a maximal weight loss of approximately 15% of their initial body weight but quickly recovered most of the lost weight by day 13 post-challenge. These animals remained fully active and exhibited little in the way of additional symptoms. As stated above, all naïve animals were fully susceptible to both H1 and H3 challenges as shown by both the survival and weight loss data.

The survival and weight loss data in FIGS. 6 and 7 demonstrate an inherent capability of this technology platform to induce significant heterosubtypic protection against influenza viral challenge. Heterosubtypic protection against influenza in mice and other models is generally associated with live infections or live vaccines (rather than inactive immunogens) and has been shown to involve both humoral and cellular components, often recognizing conserved antigens such as NP and M1, and M2. That heterosubtypic protection has been demonstrated in this experiment using a non-replicating VLP vaccine containing only an H1 HA and an N1 NA is unexpected. It is especially noteworthy that the H3N2 virus was a swarm virus that included two drift variants of H3N2. Thus, the VLP vaccine provided protection against two variants of a different subtype of influenza virus. While additional studies are underway to determine the mechanism of heterosubtypic protection, these data demonstrate the inherent robustness of this VLP vaccine platform for providing protection against widely divergent viruses. This is of obvious importance in situations such as a pandemic threat where the available vaccine and circulating viruses may be poorly matched.

ADDITIONAL REFERENCES

The following references are hereby incorporated by reference for all that they teach.

1. Katz, J. M., W. Lim, C. B. Bridges, T. Rowe, J. Hu-Primmer, X. Lu, R. A. Abernathy, M. Clarke, L. Conn, H. Kwong, M. Lee, G. Au, Y. Y. Ho, K. H. Mak, N. J. Cox, and K. Fukuda. 1999. Antibody response in individuals infected with avian influenza A (H5N1) viruses and detection of anti-H5 antibody among household and social contacts. J Infect Dis 180:1763.
2. Peiris, J. S., W. C. Yu, C. W. Leung, C. Y. Cheung, W. F. Ng, J. M. Nicholls, T. K. Ng, K. H. Chan, S. T. Lai, W. L. Lim, K. Y. Yuen, and Y. Guan. 2004. Re-emergence of fatal human influenza A subtype H5N1 disease. Lancet 363:617.
3. Horimoto, T., N. Fukuda, K. Iwatsuki-Horimoto, Y. Guan, W. Lim, M. Peiris, S. Sugii, T. Odagiri, M. Tashiro, and Y. Kawaoka. 2004. Antigenic differences between H5N1 human influenza viruses isolated in 1997 and 2003. J Vet Med Sci 66:303.
4. Tran, T. H., T. L. Nguyen, T. D. Nguyen, T. S. Luong, P. M. Pham, V. C. Nguyen, T. S. Pham, C. D. Vo, T. Q. Le, T. T. Ngo, B. K. Dao, P. P. Le, T. T. Nguyen, T. L. Hoang, V. T. Cao, T. G. Le, D. T. Nguyen, H. N. Le, K. T. Nguyen, H. S. Le, V. T. Le, D. Christiane, T. T. Tran, J. Menno de, C. Schultsz, P. Cheng, W. Lim, P. Horby, and J. Farrar. 2004. Avian influenza A (H5N1) in 10 patients in Vietnam. N Engl J Med 350:1179.
5. Li, K. S., Y. Guan, J. Wang, G. J. Smith, K. M. Xu, L. Duan, A. P. Rahardjo, P. Puthavathana, C. Buranathai, T. D. Nguyen, A. T. Estoepangestie, A. Chaisingh, P. Auewarakul, H. T. Long, N. T. Hanh, R. J. Webby, L. L. Poon, H. Chen, K. F. Shortridge, K. Y. Yuen, R. G. Webster, and J. S. Peiris. 2004. Genesis of a highly pathogenic and potentially pandemic H5N1 influenza virus in eastern Asia. Nature 430:209.
6. Lipatov, A. S., E. A. Govorkova, R. J. Webby, H. Ozaki, M. Peiris, Y. Guan, L. Poon, and R. G. Webster. 2004. Influenza: emergence and control. J Virol 78:8951.
7. Lipatov, A. S., R. J. Webby, E. A. Govorkova, S. Krauss, and R. G. Webster. 2005. Efficacy of H5 influenza vaccines produced by reverse genetics in a lethal mouse model. J Infect Dis 191:1216.
8. Stephenson, I., K. G. Nicholson, J. M. Wood, M. C. Zambon, and J. M. Katz. 2004. Confronting the avian influenza threat: vaccine development for a potential pandemic. Lancet Infect Dis 4:499.
9. Liu, M., J. M. Wood, T. Ellis, S. Krauss, P. Seiler, C. Johnson, E. Hoffmann, J. Humberd, D. Hulse, Y. Zhang, R. G. Webster, and D. R. Perez. 2003. Preparation of a standardized, efficacious agricultural H5N3 vaccine by reverse genetics. Virology 314:580.
10. Subbarao, K., H. Chen, D. Swayne, L. Mingay, E. Fodor, G. Brownlee, X. Xu, X. Lu, J. Katz, N. Cox, and Y. Matsuoka. 2003. Evaluation of a genetically modified reassortant H5N1 influenza A virus vaccine candidate generated by plasmid-based reverse genetics. Virology 305:192.

11. Webby, R. J., D. R. Perez, J. S. Coleman, Y. Guan, J. H. Knight, E. A. Govorkova, L. R. McClain-Moss, J. S. Peiris, J. E. Rehg, E. I. Tuomanen, and R. G. Webster. 2004. Responsiveness to a pandemic alert: use of reverse genetics for rapid development of influenza vaccines. Lancet 363:1099.
12. Treanor, J. J., B. E. Wilkinson, F. Masseoud, J. Hu-Primmer, R. Battaglia, D. O'Brien, M. Wolff, G. Rabinovich, W. Blackwelder, and J. M. Katz. 2001. Safety and immunogenicity of a recombinant hemagglutinin vaccine for H5 influenza in humans. Vaccine 19:1732.
13. Stephenson, I., R. Bugarini, K. G. Nicholson, A. Podda, J. M. Wood, M. C. Zambon, and J. M. Katz. 2005. Cross-reactivity to highly pathogenic avian influenza H5N1 viruses after vaccination with nonadjuvanted and MF59-adjuvanted influenza A/Duck/Singapore/97 (H5N3) vaccine: a potential priming strategy. J Infect Dis 191:1210.
14. Nicholson, K. G., A. E. Colegate, A. Podda, I. Stephenson, J. Wood, E. Ypma, and M. C. Zambon. 2001. Safety and antigenicity of non-adjuvanted and MF59-adjuvanted influenza A/Duck/Singapore/97 (H5N3) vaccine: a randomised trial of two potential vaccines against H5N1 influenza. Lancet 357:1937.
15. Subbarao, K., B. R. Murphy, and A. S. Fauci. 2006. Development of effective vaccines against pandemic influenza. Immunity 24:5.
16. Kuper, C. F., P. J. Koornstra, D. M. Hameleers, J. Biewenga, B. J. Spit, A. M. Duijvestijn, P. J. van Breda Vriesman, and T. Sminia. 1992. The role of nasopharyngeal lymphoid tissue. Immunol Today 13:219.
17. Liang, B., L. Hyland, and S. Hou. 2001. Nasal-associated lymphoid tissue is a site of long-term virus-specific antibody production following respiratory virus infection of mice. J Virol 75:5416.
18. Zuercher, A. W., S. E. Coffin, M. C. Thurnheer, P. Fundova, and J. J. Cebra. 2002. Nasal-associated lymphoid tissue is a mucosal inductive site for virus-specific humoral and cellular immune responses. J Immunol 168:1796.
19. Brandtzaeg, P. 1989. Overview of the mucosal immune system. Curr Top Microbiol Immunol 146:13.
20. Takada, A., S. Matsushita, A. Ninomiya, Y. Kawaoka, and H. Kida. 2003. Intranasal immunization with formalin-inactivated virus vaccine induces a broad spectrum of heterosubtypic immunity against influenza A virus infection in mice. Vaccine 21:3212.
21. Tamura, S. I., H. Asanuma, Y. Ito, Y. Hirabayashi, Y. Suzuki, T. Nagamine, C. Aizawa, T. Kurata, and A. Oya. 1992. Superior cross-protective effect of nasal vaccination to subcutaneous inoculation with influenza hemagglutinin vaccine. Eur J Immunol 22:477.
22. Tumpey, T. M., M. Renshaw, J. D. Clements, and J. M. Katz. 2001. Mucosal delivery of inactivated influenza vaccine induces B-cell-dependent heterosubtypic cross-protection against lethal influenza A H5N1 virus infection. J Virol 75:5141.
23. Kang, S. M., L. Guo, Q. Yao, I. Skountzou, and R. W. Compans. 2004. Intranasal immunization with inactivated influenza virus enhances immune responses to coadministered simian-human immunodeficiency virus-like particle antigens. J Virol 78:9624.
24. Guo, L., X. Lu, S. M. Kang, C. Chen, R. W. Compans, and Q. Yao. 2003. Enhancement of mucosal immune responses by chimeric influenza HA/SHIV virus-like particles. Virology 313:502.
25. Yao, Q., R. Zhang, L. Guo, M. Li, and C. Chen. 2004. Th cell-independent immune responses to chimeric hemagglutinin/simian human immunodeficiency virus-like particles vaccine. J Immunol 173:1951.
26. Latham, T., and J. M. Galarza. 2001. Formation of wild-type and chimeric influenza virus-like particles following simultaneous expression of only four structural proteins. J Virol 75:6154.
27. Galarza, J. M., T. Latham, and A. Cupo. 2005. Virus-like particle vaccine conferred complete protection against a lethal influenza virus challenge. Viral Immunol 18:365.
28. Fromantin, C., B. Jamot, J. Cohen, L. Piroth, P. Pothier, and E. Kohli. 2001. Rotavirus 2/6 virus-like particles administered intranasally in mice, with or without the mucosal adjuvants cholera toxin and *Escherichia coli* heat-labile toxin, induce a Th1/Th2-like immune response. Virol 75:11010.
29. Harrington, P. R., B. Yount, R. E. Johnston, N. Davis, C. Moe, and R. S. Baric. 2002. Systemic, mucosal, and heterotypic immune induction in mice inoculated with Venezuelan equine encephalitis replicons expressing Norwalk virus-like particles. J Virol 76:730.
30. Shi, W., J. Liu, Y. Huang, and L. Qiao. 2001. Papillomavirus pseudovirus: a novel vaccine to induce mucosal and systemic cytotoxic T-lymphocyte responses. J Virol 75:10139.
31. Han, M. G., S. Cheetham, M. Azevedo, C. Thomas, and L. J. Salt 2006. Immune responses to bovine norovirus-like particles with various adjuvants and analysis of protection in gnotobiotic calves. Vaccine 24:317.
32. Illum, L. 1998. Chitosan and its use as a pharmaceutical excipient. Pharm Res 15:1326.
33. Illum, L., I. Jabbal-Gill, M. Hinchcliffe, A. N. Fisher, and S. S. Davis. 2001. Chitosan as a novel nasal delivery system for vaccines. Adv Drug Deliv Rev 51:81.
34. Soane, R. J., M. Hinchcliffe, S. S. Davis, and L. Illum. 2001. Clearance characteristics of chitosan based formulations in the sheep nasal cavity. Int J Pharm 217:183.
35. Baudner, B. C., M. M. Giuliani, J. C. Verhoef, R. Rappuoli, H. E. Junginger, and G. D. Giudice. 2003. The concomitant use of the LTK63 mucosal adjuvant and of chitosan-based delivery system enhances the immunogenicity and efficacy of intranasally administered vaccines. Vaccine 21:3837.
36. Fujihashi, K., T. Koga, F. W. van Ginkel, Y. Hagiwara, and J. R. McGhee. 2002. A dilemma for mucosal vaccination: efficacy versus toxicity using enterotoxin-based adjuvants. Vaccine 20:2431.
37. Mutsch, M., W. Zhou, P. Rhodes, M. Bopp, R. T. Chen, T. Linder, C. Spyr, and R. Steffen. 2004. Use of the inactivated intranasal influenza vaccine and the risk of Bell's palsy in Switzerland. N Engl J Med 350:896.
38. Baldridge, J. R., Y. Yorgensen, J. R. Ward, and J. T. Ulrich. 2000. Monophosphoryl lipid A enhances mucosal and systemic immunity to vaccine antigens following intranasal administration. Vaccine 18:2416.
39. Baldrick, P., D. Richardson, G. Elliott, and A. W. Wheeler. 2002. Safety evaluation of monophosphoryl lipid A (MPL): an immunostimulatory adjuvant. Regul Toxicol Pharmacol 35:398.
40. Baldridge, J. R., P. McGowan, J. T. Evans, C. Cluff, S. Mossman, D. Johnson, and D. Persing. 2004. Taking a Toll on human disease: Toll-like receptor 4 agonists as vaccine adjuvants and monotherapeutic agents. Expert Opin Biol Ther 4:1129.

41. Baldridge, J. GlaxoSmithKline, Personal Communication.
42. Huang, J., R. J. Garmise, T. M. Crowder, K. Mar, C. R. Hwang, A. J. Hickey, J. A. Mikszta, and V. J. Sullivan. 2004. A novel dry powder influenza vaccine and intranasal delivery technology: induction of systemic and mucosal immune responses in rats. Vaccine 23:794.
43. Mills, K. H., C. Cosgrove, E. A. McNeela, A. Sexton, R. Giemza, I. Jabbal-Gill, A. Church, W. Lin, L. Illum, A. Podda, R. Rappuoli, M. Pizza, G. E. Griffin, and D. J. Lewis. 2003. Protective levels of diphtheria-neutralizing antibody induced in healthy volunteers by unilateral priming-boosting intranasal immunization associated with restricted ipsilateral mucosal secretory immunoglobulin a. Infect Immun 71:726.
44. Wimer-Mackin, S., M. Hinchcliffe, C. R. Petrie, S. J. Warwood, W. T. Tino, M. S. Williams, J. P. Stenz, A. Cheff, and C. Richardson. 2006. An intranasal vaccine targeting both the *Bacillus anthracis* toxin and bacterium provides protection against aerosol spore challenge in rabbits. Vaccine in press.
45. Noad, R., and P. Roy. 2003. Virus-like particles as immunogens. Trends Microbiol 11:438.
46. Yao, Q., V. Vuong, M. Li, and R. W. Compans. 2002. Intranasal immunization with SIV virus-like particles (VLPs) elicits systemic and mucosal immunity. Vaccine 20:2537.
47. Pushko, P., T. M. Tumpey, F. Bu, J. Knell, R. Robinson, and G. Smith. 2005. Influenza virus-like particles comprised of the HA, NA, and M1 proteins of H9N2 influenza virus induce protective immune responses in BALB/c mice. Vaccine 23:5751.
48. Baumert, T. F., S. Ito, D. T. Wong, and T. J. Liang. 1998. Hepatitis C virus structural proteins assemble into virus-like particles in insect cells. J Virol 72:3827.
49. Yao, Q., Z. Bu, A. Vzorov, C. Yang, and R. W. Compans. 2003. Virus-like particle and DNA-based candidate AIDS vaccines. Vaccine 21:638.
50. Tacket, C. O., M. B. Sztein, G. A. Losonsky, S. S. Wasserman, and M. K. Estes. 2003. Humoral, mucosal, and cellular immune responses to oral Norwalk virus-like particles in volunteers. Clin Immunol 108:241.
51. Gomez-Puertas, P., C. Albo, E. Perez-Pastrana, A. Vivo, and A. Portela. 2000. Influenza virus matrix protein is the major driving force in virus budding. J Virol 74:11538.
52. Gheysen, D., E. Jacobs, F. de Foresta, C. Thiriart, M. Francotte, D. Thines, and M. De Wilde. 1989. Assembly and release of HIV-1 precursor Pr55gag virus-like particles from recombinant baculovirus-infected insect cells. Cell 59:103.
53. Johnson, M. C., H. M. Scobie, and V. M. Vogt. 2001. PR domain of rous sarcoma virus Gag causes an assembly/budding defect in insect cells. J Virol 75:4407.
54. Kakker, N. K., M. V. Mikhailov, M. V. Nermut, A. Burny, and P. Roy. 1999. Bovine leukemia virus Gag particle assembly in insect cells: formation of chimeric particles by domain-switched leukemia/lentivirus Gag polyprotein. Virology 265:308.
55. Luo, L., Y. Li, and C. Y. Kang. 1990. Expression of gag precursor protein and secretion of virus-like gag particles of HIV-2 from recombinant baculovirus-infected insect cells. Virology 179:874.
56. Morikawa, S., T. F. Booth, and D. H. Bishop. 1991. Analyses of the requirements for the synthesis of virus-like particles by feline immunodeficiency virus gag using baculovirus vectors. Virology 183:288.
57. Takahashi, R. H., K. Nagashima, T. Kurata, and H. Takahashi. 1999. Analysis of human lymphotropic T-cell virus type II-like particle production by recombinant baculovirus-infected insect cells. Virology 256:371.
58. Yamshchikov, G. V., G. D. Ritter, M. Vey, and R. W. Compans. 1995. Assembly of SIV virus-like particles containing envelope proteins using a baculovirus expression system. Virology 214:50.
59. Weldon, R. A., Jr., C. R. Erdie, M. G. Oliver, and J. W. Wills. 1990. Incorporation of chimeric gag protein into retroviral particles. J Virol 64:4169.
60. Andrawiss, M., Y. Takeuchi, L. Hewlett, and M. Collins 2003. Murine leukemia virus particle assembly quantitated by fluorescence microscopy: role of Gag-Gag interactions and membrane association. J Virol 77:11651.
61. Leser, G. P., and R. A. Lamb. 2005. Influenza virus assembly and budding in raft-derived microdomains: a quantitative analysis of the surface distribution of HA, NA and M2 proteins. Virology 342:215.
62. Takeda, M., G. P. Leser, C. J. Russell, and R. A. Lamb. 2003. Influenza virus hemagglutinin concentrates in lipid raft microdomains for efficient viral fusion. Proc Natl Acad Sci USA 100:14610.
63. Campbell, S. M., S. M. Crowe, and J. Mak. 2001. Lipid rafts and HIV-1: from viral entry to assembly of progeny virions. J Clin Virol 22:217.
64. Sandrin, V., and F. L. Cosset. 2006. Intracellular versus cell surface assembly of retroviral pseudotypes is determined by the cellular localization of the viral glycoprotein, its capacity to interact with Gag, and the expression of the Nef protein. J Biol Chem 281:528.
65. Salazar-Gonzalez, R. M., and S. J. McSorley. 2005. *Salmonella* flagellin, a microbial target of the innate and adaptive immune system. Immunol Lett 101:117.
66. Cuadros, C., F. J. Lopez-Hernandez, A. L. Dominguez, M. McClelland, and J. Lustgarten. 2004. Flagellin fusion proteins as adjuvants or vaccines induce specific immune responses. Infect Immun 72:2810.
67. Didierlaurent, A., I. Ferrero, L. A. Otten, B. Dubois, M. Reinhardt, H. Carlsen, R. Blomhoff, S. Akira, J. P. Kraehenbuhl, and J. C. Sirard. 2004. Flagellin promotes myeloid differentiation factor 88-dependent development of Th2-type response. J Immunol 172:6922.
68. Tsujimoto, H., T. Uchida, P. A. Efron, P. O. Scumpia, A. Verma, T. Matsumoto, S. K. Tschoeke, R. F. Ungaro, S. Ono, S. Seki, M. J. Clare-Salzler, H. V. Baker, H. Mochizuki, R. Ramphal, and L. L. Moldawer. 2005. Flagellin enhances NK cell proliferation and activation directly and through dendritic cell-NK cell interactions. J Leukoc Biol 78:888.
69. Hayashi, F., T. K. Means, and A. D. Luster. 2003. Toll-like receptors stimulate human neutrophil function. Blood 102:2660.
70. Hayashi, F., K. D. Smith, A. Ozinsky, T. R. Hawn, E. C. Yi, D. R. Goodlett, J. K. Eng, S. Akira, D. M. Underhill, and A. Aderem. 2001. The innate immune response to bacterial flagellin is mediated by Toll-like receptor 5. Nature 410:1099.
71. Gewirtz, A. T., P. O. Simon, Jr., C. K. Schmitt, L. J. Taylor, C. H. Hagedorn, A. D. O'Brien, A. S. Neish, and J. L. Madara. 2001. *Salmonella typhimurium* translocates flagellin across intestinal epithelia, inducing a proinflammatory response. J Clin Invest 107:99.
72. Means, T. K., F. Hayashi, K. D. Smith, A. Aderem, and A. D. Luster. 2003. The Toll-like receptor 5 stimulus bacterial flagellin induces maturation and chemokine production in human dendritic cells. J Immunol 170:5165.

73. Smith, K. D., E. Andersen-Nissen, F. Hayashi, K. Strobe, M. A. Bergman, S. L. Barrett, B. T. Cookson, and A. Aderem. 2003. Toll-like receptor 5 recognizes a conserved site on flagellin required for protofilament formation and bacterial motility. Nat Immunol 4:1247.
74. Honko, A. N., N. Sriranganathan, C. J. Lees, and S. B. Mizel. 2006. Flagellin is an effective adjuvant for immunization against lethal respiratory challenge with *Yersinia pestis*. Infect Immun 74:1113.
75. Jeon, S. H., T. Ben-Yedidia, and R. Arnon. 2002. Intranasal immunization with synthetic recombinant vaccine containing multiple epitopes of influenza virus. Vaccine 20:2772.
76. Levi, R., and R. Arnon. 1996. Synthetic recombinant influenza vaccine induces efficient long-term immunity and cross-strain protection. Vaccine 14:85.
77. Lee, S. E., S. Y. Kim, B. C. Jeong, Y. R. Kim, S. J. Bae, O. S. Ahn, J. J. Lee, H. C. Song, J. M. Kim, H. E. Choy, S. S. Chung, M. N. Kweon, and J. H. Rhee. 2006. A bacterial flagellin, *Vibrio vulnificus* FlaB, has a strong mucosal adjuvant activity to induce protective immunity. Infect Immun 74:694.
78. Applequist, S. E., E. Rollman, M. D. Wareing, M. Liden, B. Rozell, J. Hinkula, and H. G. Ljunggren. 2005. Activation of innate immunity, inflammation, and potentiation of DNA vaccination through mammalian expression of the TLR5 agonist flagellin. J Immunol 175:3882.
79. Ramos, H. C., M. Rumbo, and J. C. Sirard. 2004. Bacterial flagellins: mediators of pathogenicity and host immune responses in mucosa. Trends Microbiol 12:509.
80. Holsinger, L. J., and R. A. Lamb. 1991. Influenza virus M2 integral membrane protein is a homotetramer stabilized by formation of disulfide bonds. Virology 183:32.
81. Lamb, R. A., S. L. Zebedee, and C. D. Richardson. 1985. Influenza virus M2 protein is an integral membrane protein expressed on the infected-cell surface. Cell 40:627.
82. Holsinger, L. J., D. Nichani, L. H. Pinto, and R. A. Lamb. 1994. Influenza A virus M2 ion channel protein: a structure-function analysis. J Virol 68:1551.
83. Takeda, M., A. Pekosz, K. Shuck, L. H. Pinto, and R. A. Lamb. 2002. Influenza a virus M2 ion channel activity is essential for efficient replication in tissue culture. J Virol 76:1391.
84. Frace, A. M., A. I. Klimov, T. Rowe, R. A. Black, and J. M. Katz. 1999. Modified M2 proteins produce heterotypic immunity against influenza A virus. Vaccine 17:2237.
85. Neirynck, S., T. Deroo, X. Saelens, P. Vanlandschoot, W. M. Jou, and W. Fiers. 1999. A universal influenza A vaccine based on the extracellular domain of the M2 protein. Nat Med 5:1157.
86. Slepushkin, V. A., J. M. Katz, R. A. Black, W. C. Gamble, P. A. Rota, and N. J. Cox. 1995. Protection of mice against influenza A virus challenge by vaccination with baculovirus-expressed M2 protein. Vaccine 13:1399.
87. Treanor, J. J., E. L. Tierney, S. L. Zebedee, R. A. Lamb, and B. R. Murphy. 1990. Passively transferred monoclonal antibody to the M2 protein inhibits influenza A virus replication in mice. J Virol 64:1375.
88. De Filette, M., W. Min Jou, A. Birkett, K. Lyons, B. Schultz, A. Tonkyro, S. Resch, and W. Fiers. 2005. Universal influenza A vaccine: optimization of M2-based constructs. Virology 337:149.
89. De Filette, M., A. Ramne, A. Birkett, N. Lycke, B. Lowenadler, W. Min Jou, X. Saelens, and W. Fiers. 2006. The universal influenza vaccine M2e-HBc administered intranasally in combination with the adjuvant CTA1-DD provides complete protection. Vaccine 24:544.
90. Fiers, W., M. De Filette, A. Birkett, S. Neirynck, and W. Min Jou. 2004. A "universal" human influenza A vaccine. Virus Res 103:173.
91. Liu, W., Z. Peng, Z. Liu, Y. Lu, J. Ding, and Y. H. Chen. 2004. High epitope density in a single recombinant protein molecule of the extracellular domain of influenza A virus M2 protein significantly enhances protective immunity. Vaccine 23:366.
92. Fan, J., X. Liang, M. S. Horton, H. C. Perry, M. P. Citron, G. J. Heidecker, T. M. Fu, J. Joyce, C. T. Przysiecki, P. M. Keller, V. M. Garsky, R. Ionescu, Y. Rippeon, L. Shi, M. A. Chastain, J. H. Condra, M. E. Davies, J. Liao, E. A. Emini, and J. W. Shiver. 2004. Preclinical study of influenza virus A M2 peptide conjugate vaccines in mice, ferrets, and rhesus monkeys. Vaccine 22:2993.
93. Ionescu, R. M., C. T. Przysiecki, X. Liang, V. M. Garsky, J. Fan, B. Wang, R. Troutman, Y. Rippeon, E. Flanagan, J. Shiver, and L. Shi. 2006. Pharmaceutical and immunological evaluation of human papillomavirus viruslike particle as an antigen carrier. J Pharm Sci 95:70.
94. Hatziioannou, T., E. Delahaye, F. Martin, S. J. Russell, and F. L. Cosset. 1999. Retroviral display of functional binding domains fused to the amino terminus of influenza hemagglutinin. Hum Gene Ther 10:1533.
95. Li, Z. N., S. N. Mueller, L. Ye, Z. Bu, C. Yang, R. Ahmed, and D. A. Steinhauer. 2005. Chimeric influenza virus hemagglutinin proteins containing large domains of the *Bacillus anthracis* protective antigen: protein characterization, incorporation into infectious influenza viruses, and antigenicity. J Virol 79:10003.
96. Haynes, J. R., S. X. Cao, B. Rovinski, C. Sia, O. James, G. A. Dekaban, and M. H. Klein. 1991. Production of immunogenic HIV-1 viruslike particles in stably engineered monkey cell lines. AIDS Res Hum Retroviruses 7:17.
97. Rovinski, B., J. R. Haynes, S. X. Cao, O. James, C. Sia, S. Zolla-Pazner, T. J. Matthews, and M. H. Klein. 1992. Expression and characterization of genetically engineered human immunodeficiency virus-like particles containing modified envelope glycoproteins: implications for development of a cross-protective AIDS vaccine. J Virol 66:4003.
98. Fynan, E. F., R. G. Webster, D. H. Fuller, J. R. Haynes, J. C. Santoro, and H. L. Robinson. 1995. DNA vaccines: a novel approach to immunization. Int J Immunopharmacol 17:79.
99. Fynan, E. F., R. G. Webster, D. H. Fuller, J. R. Haynes, J. C. Santoro, and H. L. Robinson. 1993. DNA vaccines: protective immunizations by parenteral, mucosal, and gene-gun inoculations. Proc Natl Acad Sci USA 90:11478.
100. Kodihalli, S., J. R. Haynes, H. L. Robinson, and R. G. Webster. 1997. Cross-protection among lethal H5N2 influenza viruses induced by DNA vaccine to the hemagglutinin. J Virol 71:3391.
101. Robinson, H. L., S. Lu, D. M. Feltquate, C. T. Tones, J. Richmond, C. M. Boyle, M. J. Morin, J. C. Santoro, R. G. Webster, D. Montefiori, Y. Yasutomi, N. L. Letvin, K. Manson, M. Wyand, and J. R. Haynes. 1996. DNA vaccines. AIDS Res Hum Retroviruses 12:455.
102. Drape, R. J., M. D. Macklin, L. J. Barr, S. Jones, J. R. Haynes, and H. J. Dean. 2006. Epidermal DNA vaccine for influenza is immunogenic in humans. Vaccine in press.

103. Kretzchmar, E., R. Geyer, and H. D. Klenk. 1994. Baculovirus infection does not alter N-glycosylation in *Spodoptera frugiperda* cells. Biol Chem Hoppe Seyler 375:23.
104. Lu, D., and A. J. Hickey. 2005. Liposomal dry powders as aerosols for pulmonary delivery of proteins. AAPS PharmSciTech 6:E641.
105. Cowdery, S., M. Frey, S. Orlowski, and A. Gray. 1976. Stability characteristics of freeze-dried human live virus vaccines. Dev Biol Stand 36:297.
106. Peetermans, J., G. Colinet, A. Bouillet, E. D'Hondt, and J. Stephenne. 1976. Stability of live, freeze-dried virus vaccines. Dev Biol Stand 36:291.
107. Yannarell, D. A., K. M. Goldberg, and R. N. Hjorth. 2002. Stabilizing cold-adapted influenza virus vaccine under various storage conditions. J Virol Methods 102:15.
108. Sampson, H. A., J. Bernhisel-Broadbent, E. Yang, and S. M. Scanlon. 1991. Safety of casein hydrolysate formula in children with cow milk allergy. J Pediatr 118:520.
109. Gambaryan A, A. Tuzikov, G. Pazynina, N. Bovin, A. Balish, and A. Klimov. 2005. Evolution of the receptor binding phenotype of influenza A (H5) viruses. Virology (electronic publication ahead of print version).
110. Suzuki, Y, 2005. Sialobiology of Influenza: Molecular Mechanism of Host Range Variation of Influenza Viruses. Biological and Pharmaceutical Bulletin 28:399-408.

111. Murphy, B. R., R. G. Webster. 1996. Orthomyxoviruses. In: Fields B N, Knipe D M, Howley P M, et al., eds. Fields virology. 3rd ed. Philadelphia, Pa.: Lippincott-Raven Publishers, 1397-445.

112. Clements M. L., R. F. Betts, E. L. Tierney, B. R. Murphy. 1986. Serum and nasal wash antibodies associated with resistance to experimental challenge with influenza A wild-type virus. J Clin Microbiol 24:157-60.

113. Couch R. B., J. A. Kasel. 1983. Immunity to influenza in man. Ann Rev Microbiol 37:529-49.

What we claim is:

1. A chimeric influenza virus-like particle (VLP) comprising a gag poiypeptide, an influenza hemagglutinin polypeptide, and an influenza neuraminidase polypeptide, wherein said VIP does not comprise influenza matrix M1 protein or fragments thereof; and wherein the hemagglutinin polypeptide subtype is selected from the group consisting of H1, H3, and H5.

2. The chimeric influenza virus-like particle of claim 1, wherein said gag polypeptide is from a retrovirus selected from the group consisting of: murine leukemia virus, human immunodeficiency virus, Alpharetroviruses, Betaretroviruses, Gammaretroviruses, Deltaretroviruses and Lentiviruses.

3. The chimeric influenza virus-like particle of claim 2, wherein said gag polypeptide is from a murine leukemia virus.

4. The chimeric influenza virus-like particle of claim 1, wherein said hemagglutinin polypeptide is covalently linked to an additional influenza antigen, wherein said antigen is not M1 or fragments thereof.

5. The chimeric influenza virus-like particle of claim 4, where said additional influenza antigen is an influenza virus M2 epitope.

6. The chimeric influenza virus-like particle of claim 5, where said influenza virus M2 epitope is covalently linked to the N-terminus of the hemagglutinin polypeptide.

7. The chimeric influenza virus-like particle of claim 1, wherein said neuraminidase polypeptide is covalently linked to an additional influenza antigen, wherein said antigen is not M1 or fragments thereof.

8. The chimeric influenza virus-like particle of claim 7, where said additional antigen is an influenza virus M2 epitope.

9. The chimeric influenza virus-like particle of claim 1, further comprising an adjuvant in admixture with said virus-like particle, wherein said adjuvant is not influenza M1 protein or fragments thereof.

10. The chimeric influenza virus-like particle of claim 9, wherein said adjuvant is located inside said virus-like particle.

11. The chimeric influenza virus-like particle of claim 10, wherein said adjuvant is covalently linked to said gag polypeptide.

12. The chimeric influenza virus-like particle of claim 9, wherein said adjuvant is located outside said virus-like particle.

13. The chimeric influenza virus-like particle of claim 12, wherein said adjuvant is covalently linked to said hemagglutinin polypeptide.

14. The chimeric influenza virus-like particle of claim 12, wherein said adjuvant is covalently linked to said neuraminidase polypeptide.

15. The chimeric influenza virus-like particle of claim 9, wherein said adjuvant comprises an adjuvant-active fragment of flagellin.

16. An chimeric influenza virus-like particle expression vector system, wherein said expression vector system comprises: a first nucleotide sequence encoding a gag poiypeptide, a second nucleotide sequence encoding an infiuenza neuraminidase polypeptide, and a third nucleotide sequence encoding an influenza hemagqlutinin poiypeptide, wherein the hernagglutinin polypeptide subtype is selected from the group consisting of H1, H3, and H5, and wherein a nucleotide sequence encoding influenza matrix M1 protein or fragments thereof is not provided; wherein upon expression in a cellular host, said poiypeptides form a chimeric influenza virus-like particie.

17. The chimeric influenza virus-like particle expression system of claim 14, wherein said first, second, and third nucleotide sequences are in a single expression vector.

18. The chimeric influenza virus-like particle expression system of claim 17, wherein said first, second, and third nucleotide sequences are operably linked to a single promoter.

19. The chimeric influenza virus-like particle expression system of claim 14, wherein said first, second, and third nucleotide sequences are in multiple expression vectors.

20. A method for producing a chimeric influenza virus-like particle, comprising:
  (a) providing one or more expression vectors, together which express a gag polypeptide, an influenza hemagglutinin polypeptide, and an influenza neuraminidase polypeptide; wherein influenza matrix M1 protein or fragments thereof are not provided and wherein the hemagglutinin polypeptide is from a subtype selected from the group consisting of H1, H3, and H5;
  (b) introducing said one or more expression vectors into a cell in a media;
  (c) expressing said gag polypeptide, hemagglutinin polypeptide, and neuraminidase polypeptide to produce said chimeric influenza virus-like particle (VLP); and
  (d) recovering and purifying said resulting chimeric VLPs.

21. The method of claim 20, wherein said expression vector is a viral vector.

22. The method of claim 21, wherein said viral vector is selected from the group consisting of: a baculovirus, an adenovirus, a herpesvirus, a poxvirus and a retrovirus.

23. The method of claim 22, wherein said viral vector is a baculovirus.

24. The method of claim 20, wherein said cell is selected from the group consisting of: an insect cell and a mammalian cell.

25. The method of claim 24, wherein said cell is an insect cell.

26. The method of claim 20, wherein said expression vector is a baculovirus and said cell is an insect cell.

27. A method for eliciting an immune response against influenza virus comprising administering to a subject a chimeric influenza virus-like particle (VLP), thereby inducing an immune response against influenza virus in the subject, wherein said VLP comprises:

a) a Gag polypeptide,
b) an influenza hemagglutinin polypeptide, and
c) an influenza neuraminidase polypeptide,
wherein said particle does not comprise influenza matrix M1 polypeptide or fragments thereof, wherein the hemaggiutinin polypeptide subtype is selected from the group consisting of H1, H3, and H5, and wherein the administering method is selected from the group consisting of subcutaneous delivery, transcutaneous delivery, intradermal delivery, subdermal delivery, intramuscular delivery, intraperitoneal delivery, and intravenous delivery.

28. A pharmaceutical composition comprising an immunogenic amount of the VLP of claim 1.

29. The pharmaceutical composition of claim 28, further comprising a pharmaceutically acceptable carrier.

30. The pharmaceutical composition of claim 28, wherein the neuraminidase polypeptide is from influenza A.

31. The pharmaceutical composition of claim 28, wherein the neuraminidase polypeptide is from influenza B.

32. A method for eliciting a protective immune response against influenza viral infection comprising administering to a subject in need thereof a therapeutically effective amount of a chimeric influenza virus-like particle (VLP), thereby inducing a protective immune response against influenza virus in the subject, wherein said VLP comprises:
a) a Gag polypeptide,
b) an influenza hemnagglutinin polypeptide, and
c) an influenza neuraminidase polypeptide,
wherein said particle does not comprise influenza matrix M1 polypeptide or fragments thereof, wherein the hemagglutinin polypeptide subtype is selected from the group consisting of H1, H3, and H5, and wherein the administering method is selected from the group consisting of subcutaneous delivery, transcutaneous delivery, intradermal delivery, subdermal delivery, intramuscular delivery, intraperitoneal delivery, and intravenous delivery.

33. The method of claim 32, wherein the protective immune response includes protection against heterosubtypic or drift variants.

34. The method of claim 33, wherein the heterosubtypic protection includes protection against H2, H3, H5, H7 or H9 influenza viruses and the hemagglutinin polypeptide is an H1 subtype.

35. The method of claim 33, wherein the heterosubtypic protection includes protection against H2, H5, H7 or H9 influenza viruses and the hemagglutinin poiypeptide is an H3 subtype.

36. The method of claim 33, wherein the heterosubtypic protection includes protection against H1, H2, H3, H7 or H9 influenza viruses and the hemagglutinin polypeptide is an H5 subtype.

37. The method of claim 33, wherein the heterosubtypic protection includes protection against H1 influenza viruses and the hemagglutinin polypeptide is an H5 subtype.

38. The method of claim 33, wherein the neterosubtypic protection includes protection, against H3 influenza viruses and the hemagglutinin polypeptide is an H1 subtype.

39. The method of claim 33, wherein the heterosubtypic protection includes protection against N2 influenza viruses and the neuraminidase polypeptide is an N1 subtype.

40. The method of claim 33, wherein the heterosubtypic protection includes protection against H3N2 influenza viruses and the hemagglutinin polypeptide is an H1 subtype and the neuraminidase polypeptide is an N1 subtype.

41. The method of claim 32, wherein the protective immune response includes homotypic protection.

42. The method of claim 41, wherein the homotypic protection includes protection against drift variants of the hemagglutinin polypeptide.

43. The method of claim 41, wherein the hemagglutinin polypeptide is an H1 subtype.

44. The method of claim 41, wherein the homotypic protection includes protection against drift variants of the neuraminidase polypeptide.

45. The method of claim 43, wherein the neuraminidase polypeptide is an N1 subtype.

46. The method of claim 32, wherein the protective immune response inciiudes protection against drift variants of the influenza hemaggiutinin polypeptide.

47. The method of claim 32, wherein the protective immune response includes protection against drift variants of the influenza neuraminidase polypeptide.

* * * * *